United States Patent [19]

Dean

[11] Patent Number: 5,160,363

[45] Date of Patent: Nov. 3, 1992

[54] HERBICIDAL SULFONAMIDES

[75] Inventor: Robert T. Dean, Hudson Oaks, Tex.

[73] Assignee: E. I. du Pont de Nemours and Company, Wilmington, Del.

[21] Appl. No.: 601,801

[22] PCT Filed: May 11, 1989

[86] PCT No.: PCT/US89/01953

§ 371 Date: Nov. 2, 1990

§ 102(e) Date: Nov. 2, 1990

Related U.S. Application Data

[63] Continuation-in-part of Ser. No. 193,510, May 12, 1988, abandoned.

[51] Int. Cl.$^5$ ............... C07D 239/69; A01N 43/54

[52] U.S. Cl. ..................... 71/92; 544/332; 544/323; 544/321

[58] Field of Search ............ 71/92; 544/332, 323, 544/321

[56] References Cited

FOREIGN PATENT DOCUMENTS 0044807  1/1982  European Pat. Off. .
0084020  7/1983  European Pat. Off. .
0162723 11/1985  European Pat. Off. .
0205348 12/1986  European Pat. Off. .

Primary Examiner—John M. Ford

[57] ABSTRACT

The novel compounds of Formula I are active as pre-emergent and/or post-emergent herbicides or plant growth regulants. Some of the compounds of the invention show safety to sugarbeets.

34 Claims, No Drawings

HERBICIDAL SULFONAMIDES

CROSS REFERENCE TO RELATED APPLICATION

This application is a continuation-in-part of U.S. Ser. No. 07/193,510 which was filed May 12, 1988, and is now abandoned.

BACKGROUND OF THE INVENTION

Herbicidal sulfonylureas are well known in the art. Exemplary of the patent literature teaching substituted phenyl sulfonylureas are the following: U.S. Pat. Nos. 4,383,113; 4,394,506; 4,478,635; 4,515,626; 4,659,369; 4,678,498; 4,705,556; and 4,710,221; EP-A-235,449; and South African Patent Applications 84/2722 and 84/5216.

SUMMARY OF THE INVENTION

This application pertains to novel compounds of Formula I, agriculturally suitable compositions containing them and their method-of-use as preemergent and/or postemergent herbicides or plant growth regulants.

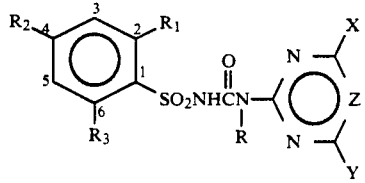

wherein
R is H or $CH_3$;
$R_1$ is $NO_2$, $CO_2R_4$, $C(O)R_5$, $S(O)_2R_6$,

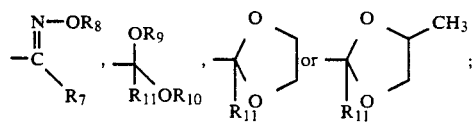

$R_2$ is

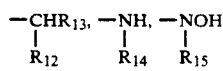

or CHO;
$R_3$ is H, $OCH_3$, $CH_3$ or Cl;
$R_4$ is $C_1$–$C_3$ alkyl, $C_2$–$C_4$ alkoxyalkyl, $C_2$–$C_3$ haloalkyl, allyl or propargyl;
$R_5$ is $C_1$–$C_3$ alkyl, $C_2$–$C_4$ alkoxyalkyl, $C_3$–$C_4$ cycloalkyl or cyclopropylmethyl;
$R_6$ is $C_1$–$C_3$ alkyl or $C_2$–$C_4$ alkoxyalkyl;
$R_7$ is $C_1$–$C_3$ alkyl, $C_2$–$C_4$ alkoxyalkyl, $C_3$–$C_4$ cycloalkyl, cyclopropylmethyl, $C_1$–$C_2$ alkoxy, CN or Cl;
$R_8$ is $C_1$–$C_3$ alkyl;
$R_9$ and $R_{10}$ are independently $C_1$–$C_2$ alkyl;
$R_{11}$ is H or $CH_3$;
$R_{12}$ is H or $CH_3$;
$R_{13}$ is CN, SCN, $NH_2$, $NHCH_3$, $N(CH_3)_2$, $NHC(O)CH_3$ or $W_2R_{16}$;
$R_{14}$ is $C_1$–$C_3$ alkyl, $C_2$–$C_4$ alkoxyalkyl or $C_2$–$C_3$ haloalkyl;
$R_{15}$ is H, $C_1$–$C_3$ alkyl, $C_2$–$C_4$ alkoxyalkyl or $C_2$–$C_3$ haloalkyl;
$R_{16}$ is H, $C_1$–$C_6$ alkyl, $C_3$–$C_4$ cycloalkyl or $C_4$–$C_5$ cycloalkylalkyl;
$W_2$ is O or S;
X is $C_1$–$C_2$ alkyl, $OCH_3$, Cl, or $OCF_2H$;
Y is H, $CH_3$, $C_1$–$C_2$ alkoxy, $NHCH_3$, or $N(CH_3)_2$; and
Z is CH or N;
and their agriculturally suitable salts; provided that
1) when X is Cl, then Z is CH and Y is $OCH_3$, $OC_2H_5$, $NHCH_3$, or $N(CH_3)_2$;
2) when X is $OCF_2H$, then Z is CH and $R_2$ is

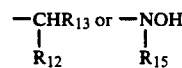

3) when $R_2$ is

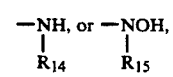

then $R_1$ is $CO_2R_4$;
4) When $R_{16}$ is H, $W_2$ is O.

In the above definitions, the term "alkyl," used either alone or in compound words such as "alkoxyalkyl" or "haloalkyl," includes straight chain or branched alkyl, e.g., methyl, ethyl, n-propyl or isopropyl.

Alkoxy includes methoxy, ethoxy, n-propyloxy and isopropyloxy.

Alkoxyalkyl includes methoxymethyl through the different methoxypropyl and propyloxymethyl isomers.

Cycloalkyl includes cyclopropyl and cyclobutyl.

$C_4$–$C_5$ cycloalkylalkyl means cyclopropylmethyl through cyclopropylethyl or cyclobutylmethyl.

The term "halogen," either alone or in compound words such as "haloalkyl," means fluorine, chlorine, bromine or iodine. Further, when used in compound words such as "haloalkyl," said alkyl may be partially or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$–$C_j$ prefix where i and j are numbers from 1 to 5. For example, $C_1$–$C_3$ alkyl would designate methyl through the propyl isomers; $C_2$ alkoxyalkyl would designate $CH_2OCH_3$; $C_4$ alkoxyalkyl would designate the various isomers of an alkyl group substituted with a alkoxy group contianing a total of 4 carbon atoms, examples including but not limited to $CH_2OCH_2CH_2CH_3$, $CH_2OCH(CH_3)_2$, $CH(CH_3)OCH_2CH_3$, $CH(CH_2CH_3)OCH_3$, $CH_2CH_2OCH_2CH_3$ and $CH_2CH_2CH_2OCH_3$.

Preferred compounds for reasons of increased ease of synthesis and/or greater herbicidal efficacy are:
1) Compounds of Formula I where
   R is H; and
   $R_3$ is H.
2) Compounds of Preferred 1 where
   $R_4$ is $CH_3$, $CH_2CH_3$ or $CH_2OCH_3$;
   $R_5$ is $C_1$–$C_3$ alkyl, cyclopropyl, cyclopropylmethyl or $CH_2OCH_3$;
   $R_6$ is $C_1$–$C_3$ alkyl or $CH_2OCH_3$;
   $R_7$ is $C_1$–$C_3$ alkyl, cyclopropyl, cyclopropylmethyl or $CH_2OCH_3$; and
   $R_{16}$ is H, or $C_1$–$C_3$ alkyl.
3) Compounds Preferred 2 where $R_2$ is 4) Compounds of Preferred 3 where
   $R_{13}$ is $W_2R_{16}$.
5) Compounds of Preferred 2 where
   $R_2$ is $NHR_{14}$.
6) Compounds of Preferred 2 where
   $R_2$ is

7) Compounds of Preferred 2 where
   $R_2$ is CHO.

Specifically preferred for reasons of greatest ease of synthesis and/or greatest herbicidal efficacy and/or greatest safety to sugar beets are:
   Methyl 2-[[[[(4,6-dimethoxypyrimidin-2-yl)amino]-carbonyl]amino]sulfonyl]-5-(methoxymethyl)benzoate, m.p. 182°–184° C.; and
   Methyl 2-[[[[(4, 6-dimethoxypyrimidin-2-yl)amino]carbonyl]amino]sulfonyl]-5-(hydroxymethyl)benzoate, m.p. 182°–185° C.

DETAILED DESCRIPTION OF THE INVENTION

Synthesis

The preparation of compounds of Formula I can be accomplished using a wide variety of methods well known in the art. Some of the more general methods used to prepare these materials are described below in Equations 1 and 2.

Many of the compounds of Formula I can be prepared by the coupling reaction of sulfonyl isocyanates of Formula II with heterocyclic amines of Formula III as shown below in Equation 1. Equation 1

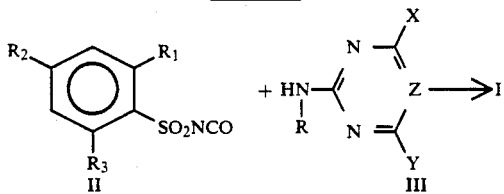

wherein,
R, $R_1$ $R_3$, X, Y and Z are as previously defined;
$R_2$ is

$R_{13}$ is CN, SCN, $W_2R_{16}$; and
$W_2$, $R_{12}$, $R_{13}$ and $R_{16}$ are as previously defined.

A useful reference for this coupling reaction is found in U.S. Pat. No. 4,394,506.

Sulfonyl isocyanates of Formula II can be prepared both from the corresponding sulfonamides of Formula V and the corresponding sulfonyl chloride of Formula VI using methods well known in the art. For a few representative examples of this process see: U.S. Pat. No. 4,238,621; Ulrich and Sayigh, *Newer Methods of Preparative Organic Chemistry*, Vol. VI, pp. 223–241, Academic Press, New York and London, W. Roerst, Ed.; Japanese Patent No. 76/126,816; U.S. Pat. No. 4,394,506; and K. Kartke, *Arch. Pharm.*, 299, 174 (1966).

A number of compounds of Formula I can be prepared by the reaction of N-phenylcarbamate derivatives of sulfonamides of Formula V with heterocyclic amines of Formula III. This method and the general procedure for the preparation of sulfonyl carbamates is taught in U.S. Pat. No. 4,443,245.

Compounds of Formula I can be prepared by the base catalyzed reaction of sulfonamides of Formula V ($R_a$ is H) with phenyl carbamates of Formula VII. This general method is widely described in the literature and a lead reference is found in EPO Publication No. 44807. Alternatively, compounds of Formula I can be prepared by the fluoride ion catalyzed coupling of N-t-butyldimethylsilyl derivatives of sulfonamides of Formula V ($R_a$ is t-butyldimethylsilyl) with phenyl carbamates of Formula VII as taught in U.S. Pat. No. 4,666,501 (Equation 2).

Equation 2

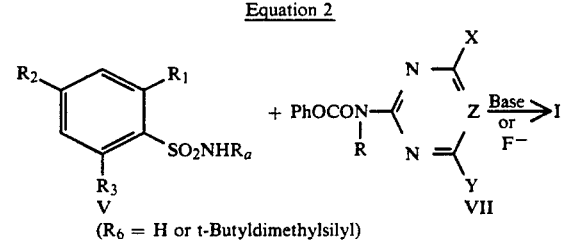

($R_6$ = H or t-Butyldimethylsilyl)

wherein,
R, $R_1$, $R_2$, $R_3$, X, Y and Z are as previously defined.

With the diversity of functional groups $R_1$, $R_2$ and $R_3$ found in this invention, a variety of methods can be used for the preparation of the numerous combinations of $R_1$, $R_2$ and $R_3$. Fortunately, there are a vast number of general synthetic methods available in the literature that enable the preparation of these compounds. With this wealth of information, one skilled in the art would be able to discern the most appropriate synthetic method by taking into account the chemical compatability of the various groups with the reaction conditions.

Sulfonamides of Formula V can be prepared using a variety of methods well known in the art. One of the most direct preparations is the reaction of ammonia with sulfonyl chlorides of Formula VI with fully assembled $R_1$, $R_2$ and $R_3$ substituents. For two useful reviews see, F. Hawking and J. S. Lawrence, "The Sulfonamides." H. K. Lewis and Co., London, 1950 and E. H. Northey, "The Sulfonamides and Allied Compounds," Reinbold Publishing Corp., New York, 1948. These intermediates can then be used to prepare compounds of Formula I as described in Equation 2.

Sulfonyl chlorides of Formula VI with less elaborated $R_1$, $R_2$ and $R_3$ substituents can be either aminated with t-butylamine to produce N-t-butyl sulfonamides of Formula V ($R_a$ is t-butyl) (Equation 3a) or by ammonia followed by silylation to produce N-t-butyldimethylsilyl sulfonamides of Formula V ($R_a$ is t-butyldimethylsilyl) (Equation 3b). Both of these derivatives are useful intermediates which allow further modifications of the $R_1$, $R_2$ and $R_3$ substituents.

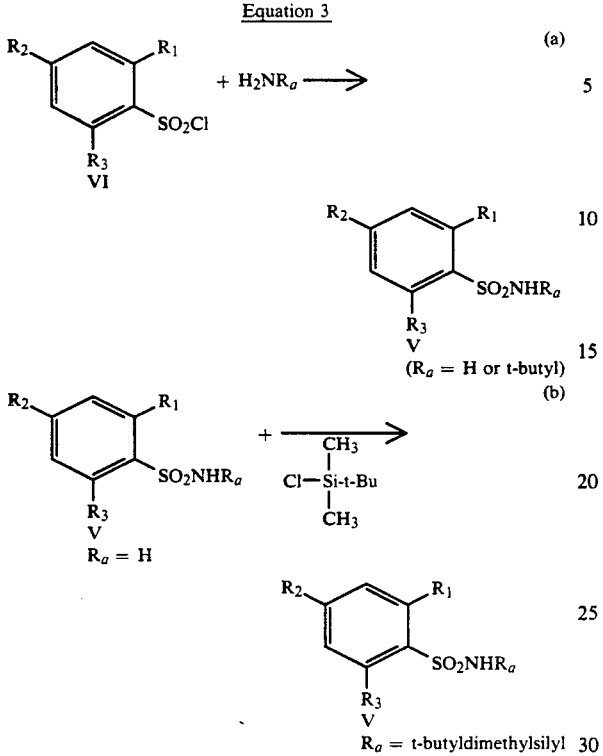

Equation 3

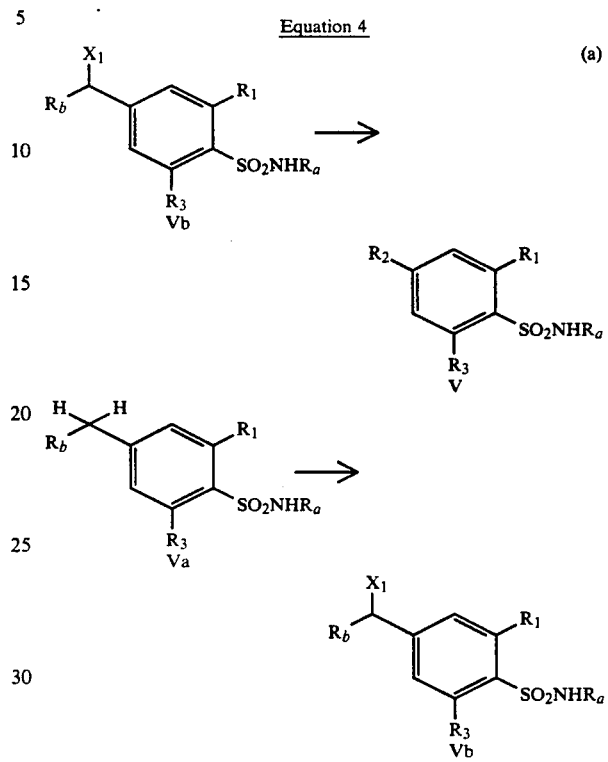

Equation 4 wherein
R$_1$, R$_2$ and R$_3$ are as previously defined.

After the R$_1$, R$_2$ and R$_3$ substituents have been assembled in the N-substituted sulfonamides of Formula V (R$_a$ is t-butyl or t-butyldimethylsilyl) these compounds are ready to be converted into the compounds of Formula I. The N-silylated sulfonamides of Formula V (R$_a$ is t-butyldimethylsilyl) can be used directly as described in Equation 2. While the N-t-butyl sulfonamides require deprotection by the action of trifluoroacetic acid before they can be taken on as described in Equation 2. The deprotection of these N-t-butyl sulfonamide derivatives is known in the literature and for an appropriate reference see: J. D. Catt and W. L. Matier, *J. Org. Chem.*, 39, 566 (1974).

A few of the strategies used to elaborate the ring substituents of the N-substituted sulfonamide derivatives of Formula V (R$_a$ is t-butyl or t-butyldimethylsilyl) into the more complicated R$_1$, R$_2$ and R$_3$ groups are shown below in Equations 4 to 7.

In terms of the R$_2$ substituents, three basic methods can be used to produce sulfonamides of Formula V:
A) From 4-methyl and ethyl precursors,
B) From 4-nitro precursors,
C) From 4-halo precursors.

A) From 4-methyl and ethyl precursors:

Most of the sulfonamides of Formula V in which the R$_2$ substituents are substituted methyl or ethyl groups are derived from the nucleophilic displacement reaction of benzylic halides (or equivalent group) of Formula Vb and an appropriate nucleophile (Equation 4a). This type of process is extensively described in the literature, for references see: Hartshorn, "Aliphatic Nucleophilic Substitution," Cambridge University Press, Cambridge, 1973; Bunton, "Nucleophilic Substitutions at a Saturated Carbon Atom," American Elsevier Publishing Company, New York, 1963; and de la Mare and Swedlund, in Patai, "The Chemistry of the Carbon-Halogen Bond," pt. 1, pp. 409–490, John Wiley & Sons, New York 1973; Parker, *Adv. Org. Chem.*, 5, (1965) 1–46.

wherein,
R$_1$ and R$_3$ are as previously defined;
R$_a$ is H, t-butyl or t-butyldimethylsilyl;
X$_1$ is Cl, Br, I, OSO$_2$Ph—4—CH$_3$ or OSO$_2$CH$_3$;
R$_b$ is H or CH$_3$;
R$_2$ is $$\begin{array}{c} \text{CHR}_{13}; \\ | \\ \text{R}_{12} \end{array}$$

and
R$_{12}$ and R$_{13}$ are as previously defined.

The benzylic halides, tosylates or mesylates of Formula Vb can be readily prepared from sulfonamides of Formula Va using any one of a number of standard techniques (Equation 4b). Some useful references can be found in: Nechvatal, *Adv. Free-Radical Chem.*, 4, 175–201 (1972); Novikov, Sevost'yanova, and Fainzil'berg, *Russ. Chem. Rev.*, 31, 671–681 (1962); Horner and Winkelmann, *Newer Methods Prep. Org. Chem.*, 3, 151–198 (1964), pp. 674–677; Djerassi, *Chem. Rev.*, 43, 271–317 (1948).

B) From 4-nitro precursors:

Sulfonamides of Formula V with R$_2$ substituents comprised of amine or hydroxylamine derivatives can be prepared from the corresponding 4-nitro sulfonamides of Formula Vc. In these cases, the 4-nitro group can be easily reduced to furnish the corresponding amine or hydroxylamine depending on reaction conditions. For a lead reference concerning these types of reductions see: March, "Advanced Organic Chemistry," pp. 1125–1126, McGraw-Hill, Inc., New York 1977; J. S. Buck and W. S. Ide, *Org. Syn.*, Coll. Vol., 1, 130 (1943). These key intermediates can then be derivatized using methods known by one skilled in the art to furnish the desired sulfonamides of Formula V (Equation 5). A good reference for these derivatizing methods is: Greene, "Protective Groups in Organic Synthesis," John Wiley and Sons, New York (1981).

Equation 5

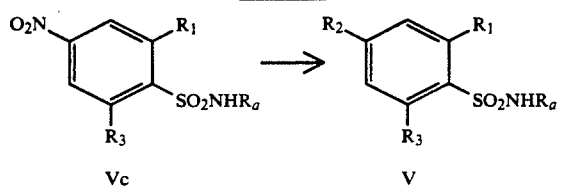

wherein,
$R_3$ is as previously defined;
$R_a$ is H, t-butyl or t-butyldimethylsilyl;
$R_2$ is $-NHR_{14}$, or $-N(R_{15})OH$, $R_{14}$ and $R_{15}$ are as previously defined;
$R_1$ is $CO_2R_4$; and
$R_4$ is as previously defined.

C) From 4-halo precursors:

Halogens, such as F, Cl or Br, substituted in the 4-position of sulfonamides of Formula Vd are susceptible to nucleophilic displacement reactions. In some cases, it is advantageous to use this strategy to prepare sulfonamides of Formula V with amine or hydroxylamine derivatives as the $R_2$ substituent (Equation 6). This type of reaction is known in the art and for reference see: Zoltewicz, *Top. Curr. Chem.*, 59, 33-64 (1975); Bunnett and Zahler, *Chem. Rev.*, 49, 273-412 (1951); Miller and Parker, *Aust. J. Chem.*, 11, 302 (1958); Berliner and Monack, *J. Amer. Chem. Soc.*, 74, 1574 (1952).

Equation 6

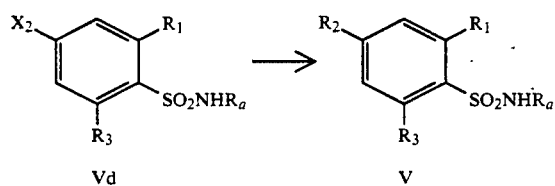

wherein,
$R_3$ is as previously defined;
$R_a$ is H, t-butyl or t-butyldimethylsilyl;
$X_2$ is F, Cl or Br;
$R_2$ is $NHR_{14}$ or $N(R_{15})OH$;
$R_{14}$ and $R_{15}$ are as previously defined; and
$R_1$ is $CO_2R_4$ and $R_4$ is as previously defined.

Many of the $R_1$ substituents found in sulfonamides of Formula V can be prepared from sulfonamides of Formula Ve ($R_a$ is t-butyl or t-butyldimethylsilyl) where $R_1$ is hydrogen. In these cases, the position ortho to the protected sulfonamide group can be deprotonated by the action of strong base. The resultant dianion can then be quenched with a variety of electrophiles which either furnish the requisite $R_1$ substituents directly or furnish precursors to these key groups. This sequence of reaction is well documented in the literature and the following references describe this technique: J. G. Lombardino, *J. Org. Chem.*, 36, (1971), 1843; P. Beak and R. A. Brown, *J. Org. Chem.*, 44, (1979) 4464; and P. Beak and V. Snieckus, *Acc. Chem. Res.*, 15, (1982) 306.

This method works well for the preparation of sulfonamides of Formula Ve in which the 4-substituent is methyl, ethyl, Cl or F (Equation 7a). In cases where the electrophile is a chloroformate derivative, and an excess of the electrophile is used, saccharin derivatives of Formula VIII (where $R_a$ is either H or t-butyl) can be obtained as the only product (Equation 7b). The ring substituents on these saccharin derivatives can be modified to the desired $R_1$, $R_2$ and $R_3$ groups in much the same manner as the ring opened sulfonamides of Formula Va and d as described in Equations 4 and 6. In addition, these saccharin derivatives can be easily converted into the sulfonamides of Formula V ($R_a$ is H or t-butyl) by methods well known in the art.

Equation 7

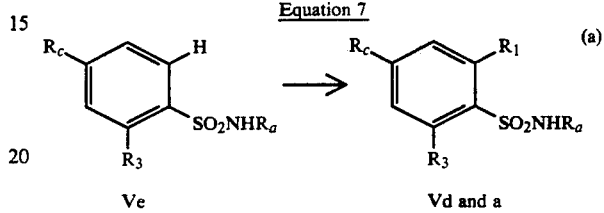
(a)

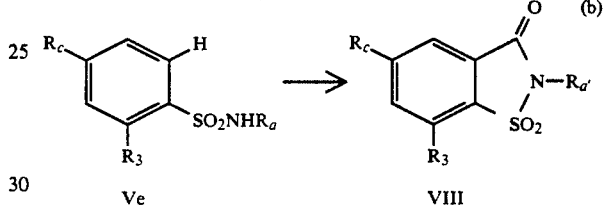
(b)

wherein,
$R_3$ is as previously defined;
$R_a$ is t-butyl or t-butyldimethylsilyl;
$R_c$ is F, Cl, $CH_3$ or $CH_2CH_3$;
Vd is as defined in Equation 6;
Va is as defined in Equation 4;
$R'_a$ is H or t-butyl; and
$R_1$ is as previously defined excluding:

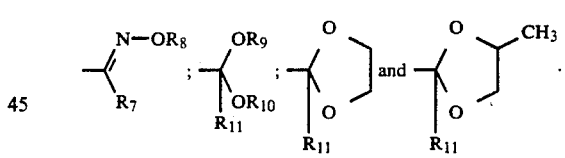

There are a variety of additional general methods in the literature that can be used for the preparation of many of the sulfonyl chlorides of Formula VI and sulfonamides of Formula V ($R_a$ is H, t-butyl or t-butyldimethylsilyl). Some representative methods are described in: H. T. Clarke et al., *Org. Synth. Coll.*, Vol. 1, 2nd Ed. 1941, p. 85; H. L. Tale and F. Sowinski, *J. Org. Chem.*, 25, 1824 (1960); and H. Meerwein et al., *Chem. Ber.*, 90, 841 (1957). Additional references can be found in U.S. Pat. Nos. 4,169,719; 4,127,405; 3,394,506; 4,435,205; 4,420,325; 4,441,910; 4,398,939; 4,456,469; 4,370,479; and EPO Publications Nos.: 23,422; 83,975; 13,480 and 95,925.

Equations 8 to 11 describe a number of specific synthetic schemes that enable the preparation of a variety of sulfonyl chlorides of Formula VI. These intermediates can then be; 1) converted directly into compounds of Formula I using procedures outlined above; 2) converted into sulfonamides of Formula V ($R_a$ is H) which in turn to compounds of Formula I; and, 3) converted into sulfonamides of Formula V ($R_a$ is t-butyl or t-butyldimethylsilyl) for further manipulations using methods already described to furnish the required $R_1$, $R_2$ and $R_3$ substituents.

From amino (or nitro) precursors:

A number of sulfonyl chlorides of Formula VIa where the ring substituents are compatible with the variety of conditions used to generate diazonium salts can be prepared from the corresponding amino derivative of Formula IX as taught in U.S. Pat. No. 4,310,346 (Equation 8). The amino derivatives of Formula IX can be obtained commercially or prepared from the corresponding nitro compounds by any one of many methods known in the literature.

Equation 8

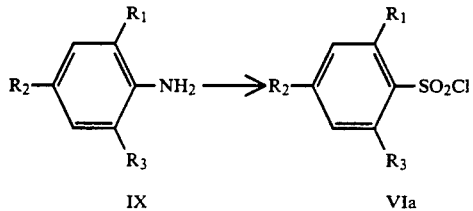

IX          VIa wherein,
$R_1$ is H or as previously defined;
$R_3$ is as previously defined;
$R_2$ can be $CH_3$, $CH_2CH_3$, Cl, F, Br, $NO_2$ and as previously defined except, not $NHR_{14}$, $N(R_{15})OH$ and $R_{13}$ is not $NH_2$, $NHCH_3$, or $N(CH_3)_2$; and
$W_2$ is not S.

From halogen precursors:

A number of sulfonyl chlorides of Formula VIb in which the ring substituents are compatible with the conditions associated with the overall process of nucleophilic displace of an activated halogen with thiolate ions followed by oxidative chlorination can be prepared from the corresponding aryl halides of Formula X (Equation 9). This sequence is taught in EPO Publication No. 94,821.

Equation 9

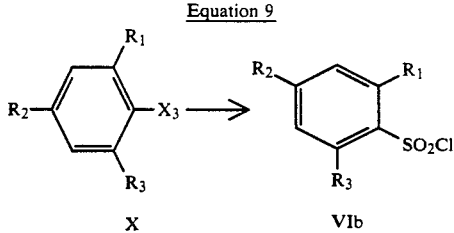

X          VIb wherein,
$R_1$ is H or previously defined except not, $C(O)R_5$,

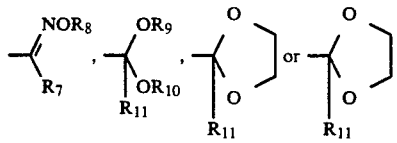

$R_2$ is $NO_2$, $CH_3$, $CH_2CH_3$, Cl;
$R_3$ is as previously defined; and
$X_3$ is F, Cl or Br.

From phenol precursors:

Sulfonyl chlorides of Formula VIc in which the ring substituents are not compatable with nucleophilic displacement reactions or oxidative chlorination conditions can be prepared from the corresponding phenol of Formula XI (Equation 10). A lead reference for this sequence is M. S. Newman and H. A. Kames, *J. Org. Chem.*, 31 (1966), 3980.

Equation 10

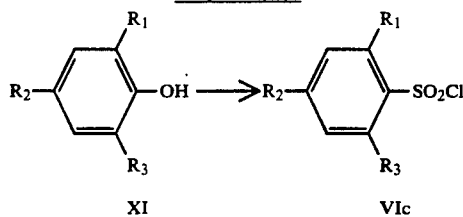

XI          VIc wherein,
$R_1$ is H or as previously described except;
$R_7$ is not $C_1-C_2$ alkoxy, CN or Cl;
$R_2$ is $NO_2$, $CH_3$, $CH_2CH_3$, Cl or Br; and
$R_3$ is as previously defined.

From aryl bromides:

Sulfonyl chlorides of Formula VId in which the ring substituents are stable to strong bases can be prepared using a sequence starting with the corresponding aryl bromides or the parent protio compound of Formula XII (Equation 11). These reactions have been extensively studies in the literature and a few lead references for this useful process can be found in: U.S. Pat. No. 4,481,029; Gschwend and Rodriguez, *Org. Reactions*, 26 (1979), 1; S. N. Bhattacharya et al., *J. Chem. Soc. C.*, (1968), 1265.

Equation 11

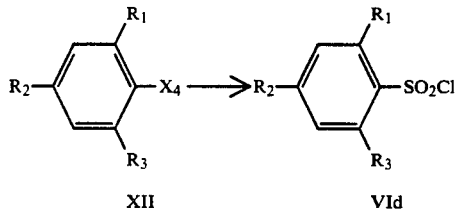

XII          VId wherein,
$R_1$ is H or as previously defined except for $NO_2$, $CO_2R_4$, $C(O)R_5$; and
$R_7$ is not $C_1-C_2$ alkoxy, CN or Cl;
$R_2$ is Cl, F, $CH_3$ or $CH_2CH_3$;
$R_3$ is as previously defined; and
$X_4$ is H or Br.

Another useful preparation of sulfonyl chlorides of Formula VI is by electrophilic chlorsulfonation of a suitably substituted aromatic ring. This technique is well known in the literature and works best for alkyl aryl ethers and alkyl aromatics. A useful reference is E. H. Huntress and F. H. Carten, *J. Am. Chem. Soc.*, 62 (1940), 511-14 and 603-4.

The heterocyclic amines of Formula III are either known or can be prepared by obvious methods by one skilled in the art.

For a review of the synthesis and reactions of 2-amino and 2-methylaminopyrimidines (III, Z=CH) see *The Chemistry of Heterocyclic Compounds*, Vol. 16, Wiley-Interscience, New York (1962). For a review of the synthesis and reactions of 2-amino- and 2-methylamino-s-triazines (III, Z=N) see *The Chemistry of Heterocyclic*

Compounds, Vol. 13, Wiley-Interscience, New York (1959), F. C. Schaefer, U.S. Pat. No. 3,154,537 and F. C. Schaefer and K. R. Huffman, *J. Org. Chem.*, 28, 1812 (1963). Heterocyclic amines, wherein X or Y is $OCF_2H$, may be prepared as described in U.S. Pat. No. 4,478,635.

The preparation of the compounds of this invention is further illustrated by the following Examples.

EXAMPLE 1

N-t-butyl 1,2-benzisothiazole-3-2H/-one 5-methyl-1,1-dioxide

To 4-methyl N-t-butylbenzenesulfonamide (10 g, 0.044 mol) in dry tetrahydrofuran (THF) (250 mL) cooled to $-78°$ C. was added dropwise n-butyllithium (35.2 mL, 2.5M, 0.088 mol) at such a rate that the temperature was kept below $-65°$ C. After all the n-butyllithium solution was added the mixture was warmed to 35° C. with a warm water bath and the mixture stirred for 2 hours. The heterogeneous mixture was then recooled to 31 78° C. and methyl chloroformate (10.2 mL, 0.132 mol) was added as rapidly as possible and the mixture was allowed to warm to room temperature. Upon warming, the mixture became homogeneous and was allowed to stirred an additional hour.

The reaction was worked-up by adding distilled water and adjusting the pH to approximately 3 using 1.0N HCl. The layers were separated and the aqueous layer was extracted with a mixture of diethyl ether and ethyl acetate. The organic layers were combined, washed with brine and dried using magnesium sulfate. The solvents were removed by rotary evaporation to leave 12.45 g of a free-flowing white solid; m.p. 85° to 88° C., and one spot by TLC.

NMR (200 MHz) $CDCl_3$ δ 7.75 (d, 1H), 7.7 (d, 1H), 7.6 (dd, 1H), 2.5 (s, 3H), 1.8 (s, 9H).

This was deemed pure enough for the next step.

EXAMPLE 2

Methyl 2-(N-t-butylsulfonyl)-5-(methoxymethyl)benzoate

The N-t-butyl saccharin derivative from Example 1 (10 g, 0.39 mol) was dissolved in a mixture of $CCl_4$ (250 mL) and $CH_2Cl_2$ (100 mL). Then N-bromosuccinimide (9.43 g, 0.53 mol) was added and the mixture was heated at reflux for approximately 2 hours after which time it was cooled to room temperature and allowed to stir for 12 hours. The reaction mixture was again heated at reflux but this time with the aid of a sun lamp. After 2 hours, the reaction was deemed complete and the mixture was concentrated on a rotary evaporator.

The residue was dissolved in diethyl ether and was immediately washed with an aqueous 5% sodium bisulfite solution. The ether layer was dried using magnesium sulfate, filtered and concentrated on a rotary evaporator to furnish 14.3 g of the crude product as a brown oil. This material was used in the next step without further purification.

This crude reaction mixture (12.17 g) was dissolved in methanol (150 mL) and then treated with a 25% sodium methoxide solution in methanol (20.44 mL) and the mixture was allowed to stir for 1 hour at 25° C. TLC analysis indicated that the reaction was incomplete so it was heated at 50° C. for approximately 2 hours. At the end of this time, the reaction was judged to be complete and the mixture was concentrated on a rotary evaporator to give a heterogeneous brown oil. The mixture was diluted with water and acidified with 1N HCl and the aqueous layer was extracted with diethyl ether. The organic layer was dried using magnesium sulfate, filtered and concentrated to furnish 8.66 g of a brown oil. This material was chromatographed on silica gel using a solvent system of ethyl acetate and hexane (1:9). This yielded 1.60 g of desired product as a white solid; m.p. 70°–72° C.

NMR (200 MHz) $CDCl_3$ δ 8.1 (d, 1H), 7.8 (s, 1H), 7.6 (d, 1H), 6.1 (bs, 1H), 4.5 (s, 2H), 4.0 (s, 3H), 3.4 (s, 3H), 1.3 (s, 9H).

EXAMPLE 3

Methyl 1-(aminosulfonyl)-5-(methoxymethyl)benzoate

The N-t-butylsulfonamide (1.6 g) prepared in Example 2 was dissolved in trifluoroacetic acid (10 mL) at 0° C. and the mixture was allowed to stir while warming to room temperature. The mixture was allowed to stir overnight after which time the trifluoroacetic acid was removed on a rotary evaporator. The crude oil was repeatedly dissolved in heptane and concentrated in vacuo to furnish a gray-brown tacky solid. The solid was triturated with n-chlorobutane and the desired product was collected as an off-white solid; m.p. 110°–115° C.

NMR (100 MHz) $D_6$ acetone δ 8.0 (dd, 1H), 7.8 (s, 1H), 7.7 (d, 1H), 6.6 (bs, 1H), 4.6 (s, 1H), 4.0 (s, 3H), 3.4 (s, 3H).

EXAMPLE 4

Methyl 2-[[[[(4,6-dimethoxypyrimidin-2-yl)amino]carbonyl-]amino]sulfonyl]-5-(methoxymethyl)benzoate The sulfonamide prepared in Example 3 (100 mg, 0.386 mmol) and phenyl 4,6-dimethoxypyrimidin-2-yl carbamate (106 mg, 0.386 mmol) were dissolved in dry acetonitrile (2 mL) and cooled to 0° C. Then 1,8-diazabicyclo[5.4.0]undec-7-ene (DBU) (0.07 mL, 0.463 mmol) was added and the mixture stirred for 1 hour. After this time ice and water were added and the solution was acidified to pH 3 with 1N HCl. The resultant solids were collected, washed with water and air dried to yield 0.145 g of a white solid that melted at 182°–184° C.

NMR (200 MHz) $D_6$ acetone δ 12.6 (bs, 1H), 9.4 (bs, 1H), 8.3 (d, 1H), 7.7 (m, 2H), 5.9 (s, 1H), 4.05 (s, 6H), 3.9 (s, 3H), 3.4 (s, 3H).

EXAMPLE 5

N-t-butyl 1,2-benzisothiazole-3-2H/-one 5-acetoxymethyl-1,1-dioxide

Silver acetate (7.5 g) was suspended in acetonitrile (50 mL) and acetic acid (30 mL) was added until the mixture became homogeneous. Then a sample of 5-bromomethyl-N-t-butylsaccharin (5.0 g) (prepared as described in Example 2) was added in acetonitrile (40 mL) and the mixture was allowed to stir for 4 days at room temperature. The mixture was filtered and the filtrate was diluted with water and extracted with ethyl acetate (3×150 mL). The ethyl acetate solutions were combined and washed once with water and then once with saturated sodium bicarbonate solution. The organics were dried with magnesium sulfate, filtered and concentrated to furnish 4 g of yellow oil which crystallized upon standing. This material was chromatographed on silica gel first using ethyl acetate and hexane (1:8) as eluent followed by a 1:1 mixture. The desired product 1.7 g was obtained as a white solid that melted at 106°–108° C.

NMR (90 MHz) CDCl$_3$ δ 7.9 (s, 1H), 7.7 (s, 2H), 5.2 (s, 2H), 2.1 (s, 3H), 1.7 (s, 9H).

EXAMPLE 6

Methyl 2-(N-t-butylsulfonyl)-5-(hydroxymethyl)benzoate

The 5-acetoxymethyl saccharin (1.7 g) prepared in Example 5 was dissolved in methanol (20 mL) and a 25% sodium methoxide in methanol solution (1.5 mL) was added and the mixture was allowed to stir for 12 hours. After this time, the mixture was poured onto an ice and water mixture and the resultant solution was extracted with ethyl acetate (3×50 mL). The organics were dried with magnesium sulfate, filtered and concentrated to afford 1.3 g of the desired product initially as a clear oil which slowly solidified on standing.

NMR (90 MHz) CDCl$_3$ δ 8.0 (d, 1H), 7.9 (d, 1H), 7.7 (dd, 1H), 6.1 (bs, 1H), 4.8 (d, 2H), 4.0 (s, 3H), 2.7 (t, 1H), 1.4 (s, 9H),

EXAMPLE 7

Methyl 2-(aminousulfonyl)-5-(hydroxymethyl)benzoate and Methyl 2-(aminosulfonyl)-5-(trifluoroacetoxymethyl)benzoate Using the same procedure described in Example 3, the N-t-butyl sulfonamide (1.2 g) prepared in Example 6 was deprotected with trifluoroacetic acid (10 mL). This furnished 1.05 g of a white solid; m.p. 98°–100° C. The solid was a mixture of the desired hydroxymethyl sulfonamide and its corresponding trifluoroacetate.

NMR (200 MHz) D$_6$ Acetone δ 8.15 (d, 1H), 7.95 (d, 1H), 7.9 (dd, 1H), 6.5 (bs, 2H), 5.6 (CH$_2$OCOCF$_3$), and 4.8 (CH$_2$OH) (s, 2H), 4.0 (s, 3H).

This mixture was used as is as trifluoroacetates such as these are cleaved during the next step.

EXAMPLE 8

Methyl 2[[[[(4,6-dimethoxypyrimidin-2-yl)amino]carbonyl-]amino]sulfonyl]-5-(hydroxymethyl)benzoate Using the same procedure described in Example 4, the mixture of sulfonamides (0.1 g) produced the desired product (0.1 g) (in which the trifluoroacetate had indeed been hydrolyzed) as a white solid; m.p. 182°–185° C.

NMR (200 MHz) D$_6$ Acetone δ 12.6 (bs, 1H), 9.4 (bs, 1H), 8.3 (d, 1H), 7.7 (m, 2H), 5.9 (s, 1H), 4.8 (s, 2H), 4.05 (s, 6H), 3.9 (s, 3H).

Using the methods described above in Equations 1 to 11, the methods (or modifications thereof) referred to by reference and Examples 1 to 8, one skilled in the art can prepare the following compounds in Tables 1 to 13.

GENERAL STRUCTURES

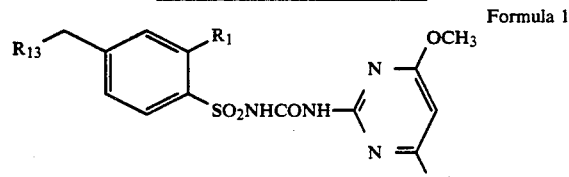

Formula 1

-continued
GENERAL STRUCTURES

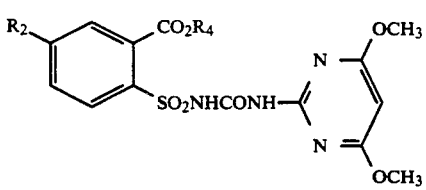

Formula 2

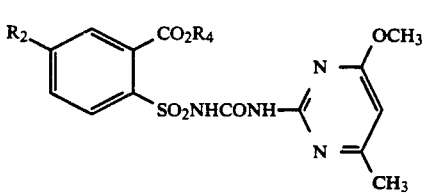

Formula 3

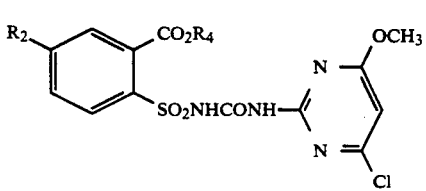

Formula 4

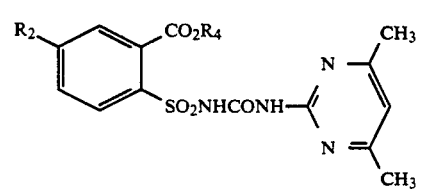

Formula 5

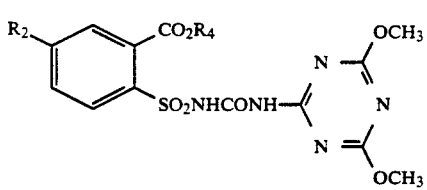

Formula 6

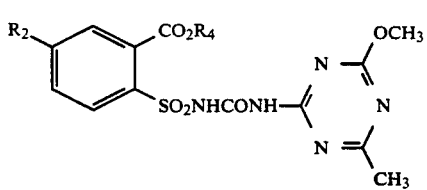

Formula 7

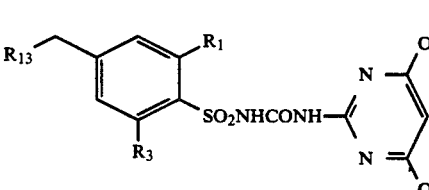

Formula 8

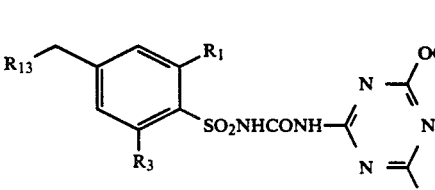

Formula 9

GENERAL STRUCTURES

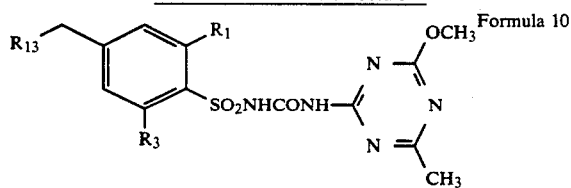

Formula 10

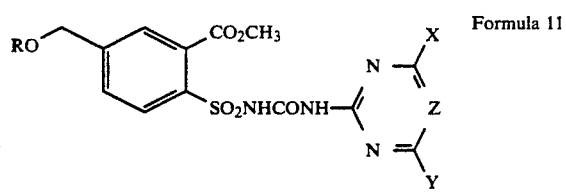

Formula 11

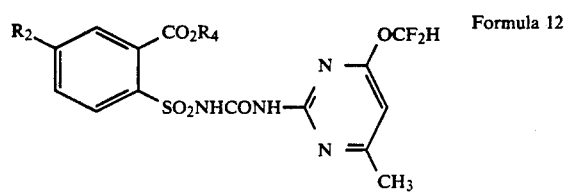

Formula 12

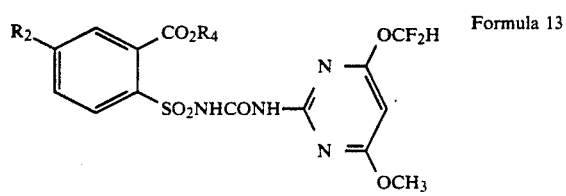

Formula 13

TABLE 1

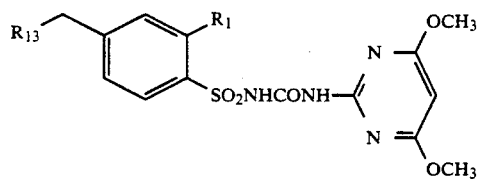

Formula I

| R₁ | R₁₃ |
|---|---|
| NO₂ | OH |
| CO₂(CH₂)₂CH₃ | OCH₃ |
| CO₂CH(CH₃)₂ | OH |
| CO₂CH₂OCH₃ | OCH₃ |
| CO₂(CH₂)₂OCH₃ | OCH₃ |
| CO₂(CH₂)₂OCH₂CH₃ | OCH₃ |
| CO₂(CH₂)₂Cl | OCH₃ |
| CO₂(CH₂)₂Br | OCH₃ |
| CO₂(CH₂)₃F | OCH₃ |
| CO₂CH₂CHCH₂ | OCH₃ |
| CO₂CH₂CCH | OCH₃ |
| C(=O)CH₃ | OH |
| C(=O)CH₂CH₃ | OH |
| C(=O)(CH₂)₂CH₃ | OH |
| C(=O)CH(CH₃)₂ | OH |
| C(=O)CH₂OCH₃ | OH |
| C(=O)CH₂OCH₂CH₃ | OCH₃ |
| C(=O)CH(CH₃)OCH₃ | OCH₃ |
| C(=O)CH(CH₃)OCH₂CH₃ | OCH₃ |
| C(=O)CH₂CH₂F | OCH₃ |
| C(=O)(CH₂)₂CH₃ | OCH₃ |
| C(=O)(CH₂)₂CH₃ | OH |
| SO₂CH₃ | OH |
| SO₂CH₂CH₃ | OCH₃ |
| SO₂(CH₂)₂CH₃ | OCH₃ |
| SO₂CH₂OCH₃ | OCH₃ |
| SO₂(CH₂)₂OCH₃ | OCH₃ |
| SO₂CH₂OCH₂CH₃ | OCH₃ |

TABLE 1-continued

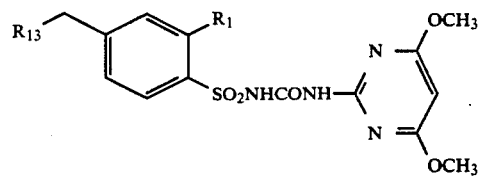

Formula I

| R₁ | R₁₃ |
|---|---|
| C(CH₃)(=NOCH₃) | OH |
| C(CH₂CH₃)(=NOCH₃) | OH |
| C(OCH₃)(=NOCH₃) | OCH₃ |
| C(OCH₂CH₃)(=NOCH₃) | OCH₃ |
| C(CN)(=NOCH₃) | OCH₃ |
| C(Cl)(=NOCH₃) | OCH₃ |
| C(CH₃)(=NOCH₂CH₃) | OCH₃ |
| C(CH₃)(=NO(CH₂)₂CH₃) | OCH₃ |
| C(CH₃OCH₃)₂ | OH |
| CH(OCH₃)₂ | OCH₃ |
| CH(OCH₂CH₂O)₂ | OCH₃ |
| CH(OCH(CH₃)CH₂O)₂ | OCH₃ |

TABLE 2

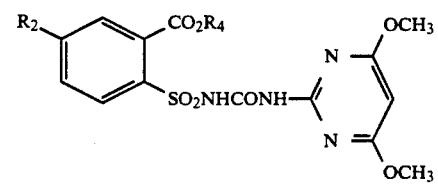

Formula 2

| R₄ | R₂ |
|---|---|
| CH₃ | CH₂CN |
| CH₃ | CH(CH₃)CN |
| CH₃ | CH₂SCN |
| CH₃ | CH(CH₃)SCN |
| CH₃ | CH₂NH₂ |
| CH₃ | CH₂NHCH₃ |
| CH₃ | CH₂N(CH₃)₂ |
| CH₃ | CH₂NHCOCH₃ |
| CH₃ | CH(CH₃)NHCOCH₃ |
| CH₃ | CH₂OH |
| CH₃ | CH(CH₃)OH |
| CH₃ | CH₂OCH₃ |
| CH₃ | CH₂OCH₂CH₃ |
| CH₃ | CH₂O(CH₂)₂CH₃ |
| CH₃ | CH₂O(CH₂)₃CH₃ |
| CH₃ | CH₂O(CH₂)₄CH₃ |
| CH₃ | CH₂OCH₂(CH₂)₄CH₃ |
| CH₃ | CH₂SCH₃ |
| CH₃ | CH₂SCH₂CH₃ |
| CH₃ | CH₂SCH(CH₃)₂ |
| CH₃ | CH₂SCH₂(CH₂)₃CH₃ |
| CH₃ | NHCH₃ |
| CH₃ | NHCH₂CH₃ |
| CH₃ | NH(CH₂)₂CH₃ |
| CH₃ | NHCH(CH₃)₂ |
| CH₃ | NHCH₂OCH₃ |
| CH₃ | NH(CH₂)₂OCH₃ |
| CH₃ | NH(CH₂)₂OCH₂CH₃ |
| CH₃ | NHCH₂CF₃ |
| CH₃ | NHCH(CH₃)CH₂OCH₃ |
| CH₃ | N(OH)H |
| CH₃ | N(OH)CH₃ |
| CH₃ | N(OH)CH₂CH₃ |
| CH₃ | N(OH)CH(CH₃)₂ |
| CH₃ | N(OH)(CH₂)₂CH₃ |
| CH₃ | N(OH)CH₂CF₃ |

TABLE 3

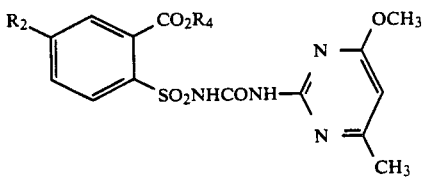

Formula 3

| $R_4$ | $R_2$ |
|---|---|
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_2CH_3$ | $CH_2OCH_2(CH_2)_3CH_3$ |
| $CH_3$ | $CH_2OCH_2(CH_2)_4CH_3$ |
| $CH_3$ | $CH_2SCH_3$ |
| $CH_3$ | $CH_2SCH_2CH_3$ |
| $CH_3$ | $CH_2SCN(CH_3)_2$ |
| $CH_3$ | $CH_2SCH_2(CH_2)_3CH_3$ |
| $CH_3$ | $NHCH_3$ |
| $CH_3$ | $NHCH_2CH_3$ |
| $CH_3$ | $NH(CH_2)_2CH_3$ |
| $CH_3$ | $NHCH(CH_3)_2$ |
| $CH_3$ | $NHCH_2OCH_3$ |
| $CH_3$ | $NH(CH_2)_2OCH_3$ |
| $CH_3$ | $NH(CH_2)_2OCH_2CH_3$ |
| $CH_3$ | $NHCH_2CF_3$ |
| $CH_3$ | $NHCH(CH_3)CH_2OCH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_3)_2$ |
| $CH_3$ | $N(OH)(CH_2)_2CH_3$ |
| $CH_3$ | $N(OH)CH_2CF_3$ |

TABLE 4

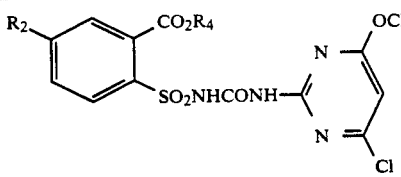

Formula 4

| $R_4$ | $R_2$ |
|---|---|
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_2CH_3$ | $CH_2OCH_2(CH_2)_3CH_3$ |
| $CH_3$ | $CH_2OCH_2(CH_2)_4CH_3$ |
| $CH_3$ | $CH_2SCH_3$ |

TABLE 4-continued

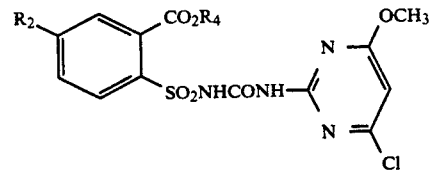

Formula 4

| $R_4$ | $R_2$ |
|---|---|
| $CH_3$ | $CH_2SCH_2CH_3$ |
| $CH_3$ | $CH_2SCH(CH_3)_2$ |
| $CH_3$ | $CH_2SCH_2(CH_2)_3CH_3$ |
| $CH_3$ | $NHCH_3$ |
| $CH_3$ | $NHCH_2CH_3$ |
| $CH_3$ | $NH(CH_2)_2CH_3$ |
| $CH_3$ | $NHCH(CH_3)_2$ |
| $CH_3$ | $NHCH_2OCH_3$ |
| $CH_3$ | $NH(CH_2)_2OCH_3$ |
| $CH_3$ | $NH(CH_2)_2OCH_2CH_3$ |
| $CH_3$ | $NHCH_2CF_3$ |
| $CH_3$ | $NHCH(CH_3)CH_2OCH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_2)_2CH_3$ |
| $CH_3$ | $N(OH)(CH_2)_2CH_3$ |
| $CH_3$ | $N(OH)CH_2CF_3$ |

TABLE 5

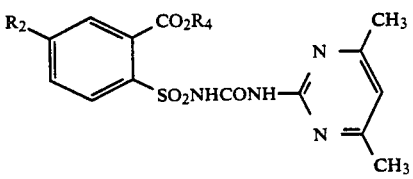

Formula 5

| $R_4$ | $R_2$ |
|---|---|
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_2CH_3$ | $CH_2OCH_2(CH_2)_3CH_3$ |
| $CH_3$ | $CH_2OCH_2(CH_2)_4CH_3$ |
| $CH_3$ | $CH_2SCH_3$ |
| $CH_3$ | $CH_2SCH_2CH_3$ |
| $CH_3$ | $CH_2SCH(CH_3)_2$ |
| $CH_3$ | $CH_2SCH_2(CH_2)_3$ |
| $CH_3$ | $NHCH_3$ |
| $CH_3$ | $NHCH_2CH_3$ |
| $CH_3$ | $NH(CH_2)_2CH_3$ |
| $CH_3$ | $NHCH(CH_3)_2$ |
| $CH_3$ | $NHCH_2OCH_3$ |
| $CH_3$ | $NH(CH_2)_2OCH_3$ |
| $CH_3$ | $NH(CH_2)_2OCH_2CH_3$ |
| $CH_3$ | $NHCH_2CF_3$ |
| $CH_3$ | $NHCH(CH_3)CH_2OCH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_3)_2$ |
| $CH_3$ | $N(OH)(CH_2)_2CH_3$ |

TABLE 5-continued

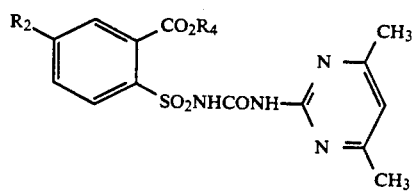

Formula 5

| $R_4$ | $R_2$ |
|---|---|
| $CH_3$ | $N(OH)CH_2CF_3$ |

TABLE 6

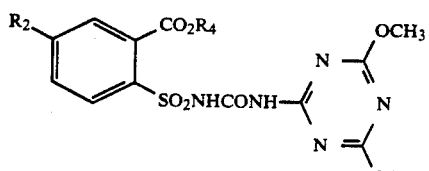

Formula 6

| $R_4$ | $R_2$ |
|---|---|
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_2CH_3$ | $CH_2OCH_2(CH_2)_3CH_3$ |
| $CH_3$ | $CH_2OCH_2(CH_2)_4CH_3$ |
| $CH_3$ | $CH_2SCH_3$ |
| $CH_3$ | $CH_2SCH_2CH_3$ |
| $CH_3$ | $CH_2SCH(CH_3)_2$ |
| $CH_3$ | $CH_2SCH_2(CH_2)_3$ |
| $CH_3$ | $NHCH_3$ |
| $CH_3$ | $NHCH_2CH_3$ |
| $CH_3$ | $NH(CH_2)_2CH_3$ |
| $CH_3$ | $NHCH(CH_3)_2$ |
| $CH_3$ | $NHCH_2OCH_3$ |
| $CH_3$ | $NH(CH_2)_2OCH_3$ |
| $CH_3$ | $NH(CH_2)_2OCH_2CH_3$ |
| $CH_3$ | $NHCH_2CF_3$ |
| $CH_3$ | $NHCH(CH_3)CH_2OCH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_3)_2$ |
| $CH_3$ | $N(OH)(CH_2)_2CH_3$ |
| $CH_3$ | $N(OH)CH_2CF_3$ |

TABLE 7

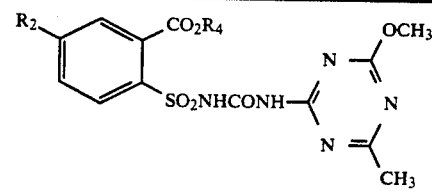

Formula 7

| $R_4$ | $R_2$ |
|---|---|
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_3$ | $CH_2OCH_2(CH_2)_4CH_3$ |
| $CH_3$ | $CH_2SCH_3$ |
| $CH_3$ | $CH_2SCH_2CH_3$ |
| $CH_3$ | $CH_2SCH(CH_3)_2$ |
| $CH_3$ | $CH_2SCH_2(CH_2)_3$ |
| $CH_3$ | $NHCH_3$ |
| $CH_3$ | $NHCH_2CH_3$ |
| $CH_3$ | $NH(CH_2)_2CH_3$ |
| $CH_3$ | $NHCH(CH_3)_2$ |
| $CH_3$ | $NHCH_2OCH_3$ |
| $CH_3$ | $NH(CH_2)_2OCH_3$ |
| $CH_3$ | $NH(CH_2)_2OCH_2CH_3$ |
| $CH_3$ | $NHCH_2CF_3$ |
| $CH_3$ | $NHCH(CH_3)CH_2OCH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_3)_2$ |
| $CH_3$ | $N(OH)(CH_2)_2CH_3$ |
| $CH_3$ | $N(OH)CH_2CF_3$ |

TABLE 8

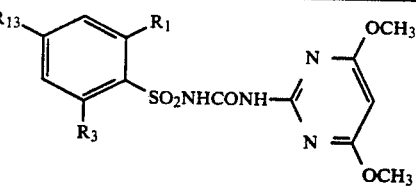

Formula 8

| $R_1$ | $R_{13}$ | $R_3$ |
|---|---|---|
| $NO_2$ | $OH$ | $OCH_3$ |
| $C(CH_3)(=NOCH_3)$ | $OH$ | $Cl$ |
| $CO_2CH_3$ | $OH$ | $Cl$ |
| $COCH_2CH_3$ | $OH$ | $Cl$ |
| $C(CH_3)(OCH_3)_2$ | $OH$ | $Cl$ |
| $CH(OCH_3)_2$ | $OH$ | $Cl$ |
| $CH(OCH_2CH_2O)$ | $OH$ | $Cl$ |
| $SO_2CH_2CH_3$ | $OH$ | $OCH_3$ |
| $NO_2$ | $OH$ | $CH_3$ |
| $NO_2$ | $OCH_3$ | $OCH_3$ |
| $C(CH_3)(=NOCH_3)$ | $OCH_3$ | $Cl$ |
| $CO_2CH_3$ | $OCH_3$ | $Cl$ |
| $COCH_2CH_3$ | $OCH_3$ | $Cl$ |
| $C(CH_3)(OCH_3)_2$ | $OCH_3$ | $Cl$ |
| $CH(OCH_3)_2$ | $OCH_3$ | $Cl$ |
| $CH(OCH_2CH_2O)$ | $OCH_3$ | $Cl$ |
| $SO_2CH_2CH_3$ | $OCH_3$ | $CH_3$ |

TABLE 8-continued

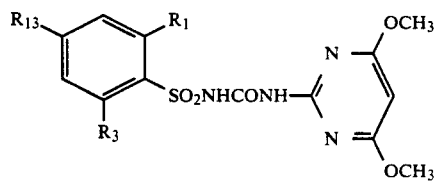

| Formula 8 | | |
|---|---|---|
| $R_1$ | $R_{13}$ | $R_3$ |
| $NO_2$ | $OCH_3$ | Cl |

TABLE 9

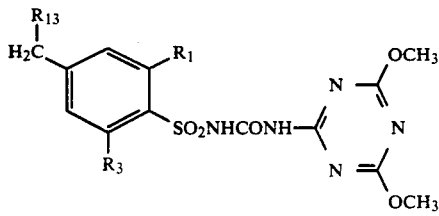

| Formula 9 | | |
|---|---|---|
| $R_1$ | $R_{13}$ | $R_3$ |
| $NO_2$ | OH | $OCH_3$ |
| $C(CH_3)(=NOCH_3)$ | OH | Cl |
| $CO_2CH_3$ | OH | Cl |
| $COCH_2CH_3$ | OH | Cl |
| $C(CH_3)(OCH_3)_2$ | OH | Cl |
| $CH(OCH_3)_2$ | OH | Cl |
| $CH(OCH_2CH_2O)_2$ | OH | Cl |
| $SO_2CH_2CH_3$ | OH | Cl |
| $NO_2$ | OH | $CH_3$ |
| $NO_2$ | $OCH_3$ | $OCH_3$ |
| $C(CH_3)(=NOCH_3)$ | $OCH_3$ | Cl |
| $CO_2CH_3$ | $OCH_3$ | Cl |
| $COCH_2CH_3$ | $OCH_3$ | Cl |
| $C(CH_3)(OCH_3)_2$ | $OCH_3$ | Cl |
| $CH(OCH_3)_2$ | $OCH_3$ | Cl |
| $CH(OCH_2CH_2O)_2$ | $OCH_3$ | Cl |
| $SO_2CH_2CH_3$ | $OCH_3$ | $CH_3$ |
| $NO_2$ | $OCH_3$ | $CH_3$ |

TABLE 10

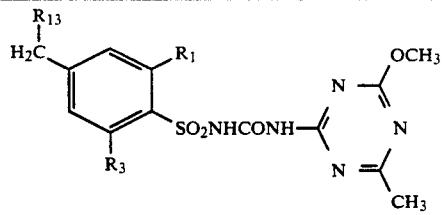

| Formula 10 | | |
|---|---|---|
| $R_1$ | $R_{13}$ | $R_3$ |
| $NO_2$ | OH | $OCH_3$ |
| $C(CH_3)(=NOCH_3)$ | OH | Cl |
| $CO_2CH_3$ | OH | Cl |
| $COCH_2CH_3$ | OH | Cl |
| $C(CH_3)(OCH_3)_2$ | OH | Cl |
| $CH(OCH_3)_2$ | OH | Cl |
| $CH(OCH_2CH_2O)_2$ | OH | Cl |
| $SO_2CH_2CH_3$ | OH | $CH_3$ |
| $NO_2$ | OH | $CH_3$ |
| $C(CH_3)(=NOCH_3)$ | $OCH_3$ | Cl |
| $CO_2CH_3$ | $OCH_3$ | Cl |
| $COCH_2CH_3$ | $OCH_3$ | Cl |
| $C(CH_3)(OCH_3)_2$ | $OCH_3$ | Cl |
| $CH(OCH_3)_2$ | $OCH_3$ | Cl |

TABLE 10-continued

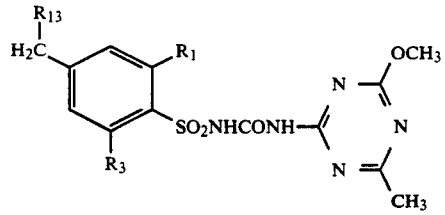

| Formula 10 | | |
|---|---|---|
| $R_1$ | $R_{13}$ | $R_3$ |
| $CH(OCH_2CH_2O)_2$ | $OCH_3$ | Cl |

TABLE 11

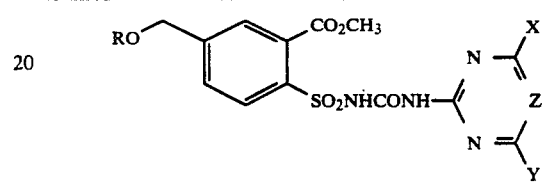

| Formula 11 | | | |
|---|---|---|---|
| R | X | Y | Z |
| H | $CH_2CH_3$ | $OCH_3$ | CH |
| H | $CH_2CH_3$ | $OCH_2CH_3$ | CH |
| H | $OCH_2CH_3$ | $OCH_2CH_3$ | CH |
| $CH_3$ | $OCH_3$ | $NHCH_3$ | N |
| $CH_3$ | $CH_3$ | $NHCH_3$ | N |

TABLE 12

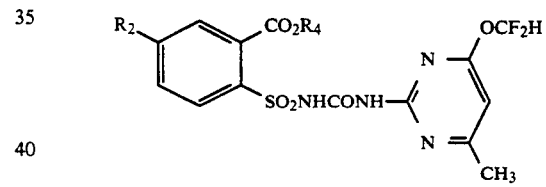

| Formula 12 | |
|---|---|
| $R_4$ | $R_2$ |
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_2CH_3$ | $CH_2OCH_2(CH_2)_3CH_3$ |
| $CH_3$ | $CH_2OCH_2(CH_2)_4CH_3$ |
| $CH_3$ | $CH_2SCH_3$ |
| $CH_3$ | $CH_2SCH_2CH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_3)_2$ |
| $CH_3$ | $N(OH)(CH_2)_2CH_3$ |
| $CH_3$ | $N(OH)CH_2CF_3$ |

TABLE 13

$$R_2\text{-}C_6H_3(CO_2R_4)(SO_2NHCONH\text{-}\text{pyrimidine with }OCF_2H\text{ and }OCH_3)$$

Formula 13

| $R_4$ | $R_2$ |
|---|---|
| $CH_3$ | $CH_2CN$ |
| $CH_3$ | $CH(CH_3)CN$ |
| $CH_3$ | $CH_2SCN$ |
| $CH_3$ | $CH(CH_3)SCN$ |
| $CH_3$ | $CH_2NH_2$ |
| $CH_3$ | $CH_2NHCH_3$ |
| $CH_3$ | $CH_2N(CH_3)_2$ |
| $CH_3$ | $CH_2NHCOCH_3$ |
| $CH_3$ | $CH(CH_3)NHCOCH_3$ |
| $CH_3$ | $CH_2OH$ |
| $CH_3$ | $CH(CH_3)OH$ |
| $CH_3$ | $CH_2OCH_3$ |
| $CH_3$ | $CH_2OCH_2CH_3$ |
| $CH_3$ | $CH_2O(CH_2)_2CH_3$ |
| $CH_3$ | $CH_2O(CH_2)_3CH_3$ |
| $CH_3$ | $CH_2O(CH_2)_4CH_3$ |
| $CH_3$ | $CH_2OCH_2(CH_2)_4CH_3$ |
| $CH_3$ | $CH_2SCH_3$ |
| $CH_3$ | $CH_2SCH_2CH_3$ |
| $CH_3$ | $N(OH)H$ |
| $CH_3$ | $N(OH)CH_3$ |
| $CH_3$ | $N(OH)CH_2CH_3$ |
| $CH_3$ | $N(OH)CH(CH_3)_2$ |
| $CH_3$ | $N(OH)(CH_2)_2CH_3$ |
| $CH_3$ | $N(OH)CH_2CF_3$ |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulations. The formulations, broadly, contain about 0.1% to 99% by weight of active ingredient(s) and at least one of (a) about 0.1% to 20% surfactant(s) and (b) about 1% to 99.9% solid and/or liquid diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual:, MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

| Wettable Powder | |
|---|---|
| Methyl 2-[[[[(4,6-dimethoxypyrimidin-2-yl)amino]carbonyl]amino]sulfonyl]-5-(methoxyethyl)-benzoate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

| | |
|---|---|
| Methyl 2-[[[[(4,6-dimethoxypyrimidin-2-yl)amino]-carbonyl]amino]sulfonyl]-5-(hydroxymethyl)-benzoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
|---|---|
| Wettable Powder of Example 10 | 5% |
| attapulgite granules (U.S.S. 20-40 mesh; 0.84-0.42 mm) | 95% |

A slurry of wettable powder containing 25% solids is sprayed on the surface of attapulgite granules in a double-cone blender. The granules are dried and packed.

EXAMPLE 12

| Extruded Pellet | |
|---|---|
| Methyl 2-[[[[(4,6-dimethoxypyrimidin-2-yl)amino]-carbonyl]amino]sulfonyl]-5-(methoxymethyl)-benzoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

| | |
|---|---|
| Methyl 2-[[[[(4,6-dimethoxypyrimidin-2-yl)amino]-carbonyl]amino]sulfonyl]-5-(hydroxymethyl)-benzoate | 1% |
| N,N-dimethylformamide | 9% |
| attapulgite granules (U.S.S. 20 to 40 sieve) | 90% |

The active ingredient is dissolved is dissolved in the solvent and the solution is sprayed upon dedusted granules in a double-cone blender. After spraying of the solution has been completed, the blender is allowed to run for a short period and then the granules are packaged.

EXAMPLE 14

| | |
|---|---|
| Methyl 2-[[[[(4,6-dimethoxypyrimidin-2-yl)amino]-carbonyl]amino]sulfonyl]-5-(methoxymethyl)-benzoate | 80% |
| wetting agent | 1% |
| crude ligninsulfonate salt (containing 5-20% of the natural sugars) | 20% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 15

| | |
|---|---|
| Methyl 2-[[[[(4,6-dimethoxypyrimidin-2-yl)amino]-carbonyl]amino]sulfonyl]-5-(hydroxymethyl)-benzoate | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| | |
|---|---|
| Methyl 2-[[[[(4,6-dimethoxypyrimidin-2-yl)amino]-carbonyl]amino]sulfonyl]-5-(methoxymethyl)-benzoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| Methyl 2-[[[[(4,6-dimethoxypyrimidin-2-yl)amino]-carbonyl]amino]sulfonyl]-5-(hydroxymethyl)-benzoate | 5% |
| water | 95% |

The salt is added directly to the water with stirring to produce the solution, which may then be packaged for use.

EXAMPLE 18

| High Strength Concentrate | |
|---|---|
| Methyl 2-[[[[(4,6-dimethoxypyrimidin-2-yl)amino]-carbonyl]amino]sulfonyl]-5-(methoxymethyl)- | 99% |

| -continued | |
|---|---|
| High Strength Concentrate | |
| benzoate | |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| Methyl 2-[[[[(4,6-dimethoxypyrimidin-2-yl)amino]-carbonyl]amino]sulfonyl]-5-(hydroxymethyl)-benzoate | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

| | |
|---|---|
| Methyl 2-[[[[(4,6-dimethoxypyrimidin-2-yl)amino]-carbonyl]amino]sulfonyl]-5-(methoxymethyl)-benzoate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| | |
|---|---|
| Methyl 2-[[[[(4,6-dimethoxypyrimidin-2-yl)amino]-carbonyl]amino]sulfonyl]-5-(hydroxymethyl)-benzoate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

| | |
|---|---|
| Methyl 2-[[[[(4,6-dimethoxypyrimidin-2-yl)amino]-carbonyl]amino]sulfonyl]-5-(methoxymethyl)-benzoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 23

| | |
|---|---|
| Methyl 2-[[[[(4,6-dimethoxypyrimidin-2-yl)amino]-carbonyl]amino]sulfonyl]-5-(hydroxymethyl)-benzoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Utility

Many compounds of this invention are particularly useful for the control of weeds in sugar beets and fodder beets. This is a crop that takes a long period to become established. In this interval, the crop seedlings must be nurtured carefully, with particular attention to weed control to prevent damage due to competition. The subject compound can be used either pre- or post-emergence and will control numerous problem weeds including galium (*Galium aparine*), pigweed (Amaranthus spp.), lambsquarters (*Chenopodium album*), wild oats (*Avena fatua*), wild radish (*Raphanus raphanistrum*), and blackgrass (*Alopecurus myosuroides*). Some of the compounds of the invention are useful for selective weed control in other crops such as soybeans. Additionally, some of these compounds are useful as plant growth regulants or as citrus abscission agents.

The rate of application of a compound from this invention is determined by a number of factors including the weeds to be controlled, weather and climate, soil type, time of application, age and size of crop and weeds, method of application (pre- or post-), etc. In general terms, the rate will vary between about 1 and 20000 g/ha, with a preferred rate of about 4 to 500 g/ha. The rate to be used in any given situation can be selected by one with ordinary skill in the art.

These compounds can and will often be used in mixtures with one or more other herbicides. They may be mixed with any other herbicides selective on beets including metamitron, phenmedipham, chloridazin, desmedipham, lenacil, ethofumesate, cycloate, diclorpmethyl, fluazifop, haloxyfop, and quinoxyfop ethyl. Or if used in soybeans, they may be advantageously mixed with compounds selective on soybeans. These compounds include, but are not restricted to: acifluorfen, alachlor, bentazon, chlorbromuron, chlorimuron ethyl, chloroxuron, diclofop, fexoaprop ethyl, imazaquin, linuron, metachlor, metribuzin, oxyfluorfen, propachlor, quinoxyfop ethyl, sethoxydim, trifluralin, vernolate, 2,4-DB, cinmethylin, imazethapyr, thiameturon methyl, haloxyfop-methyl and 2-(2'-chlorophenyl)-methyl-4,4-dimethyl-3-isoxazolidinone.

Herbicidal properties of compounds of this invention were discovered in a number of greenhouse tests. Test descriptions and results follow.

COMPOUNDS
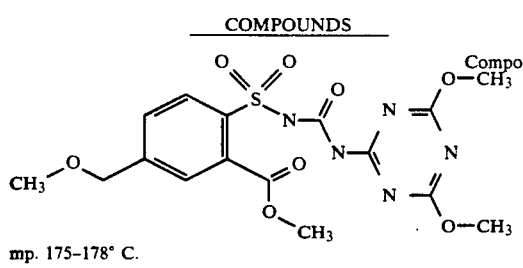
Compound 1
mp. 175–178° C.
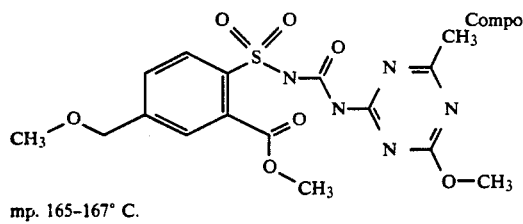
Compound 2
mp. 165–167° C.
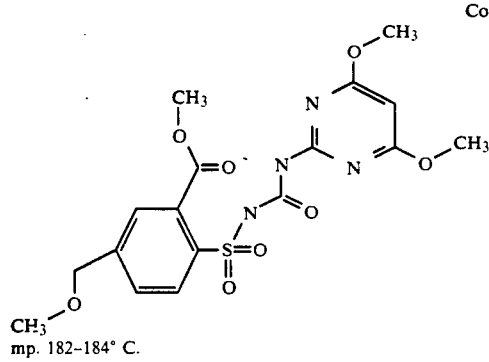
Compound 3
mp. 182–184° C.
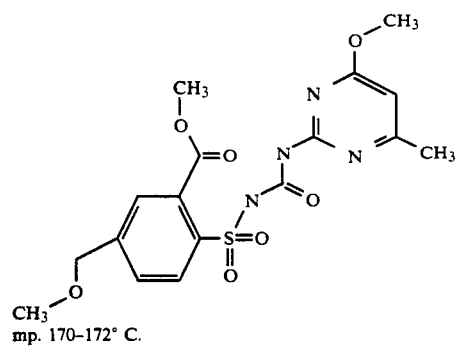
Compound 4
mp. 170–172° C.
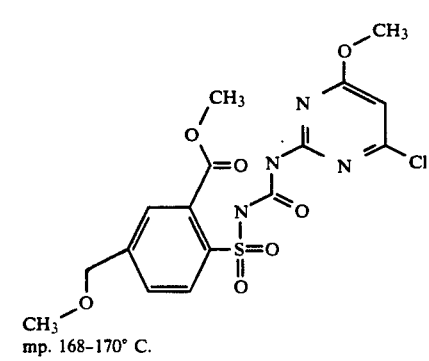
Compound 5
mp. 168–170° C.
-continued
COMPOUNDS
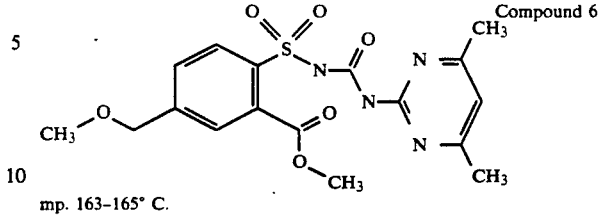
Compound 6
mp. 163–165° C.
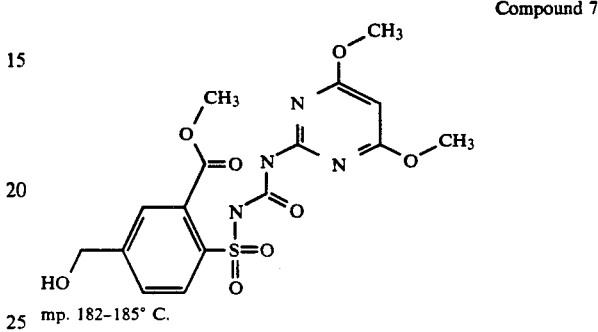
Compound 7
mp. 182–185° C.
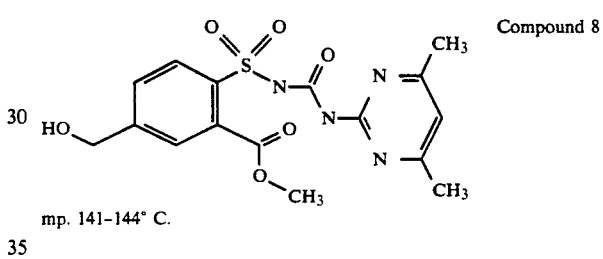
Compound 8
mp. 141–144° C.
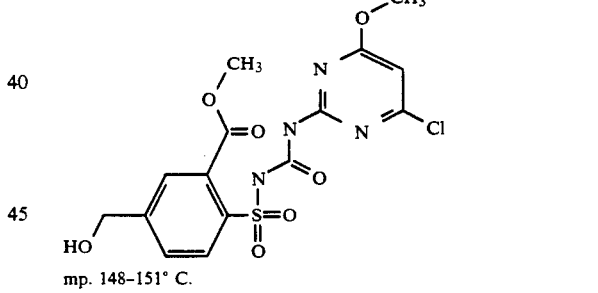
Compound 9
mp. 148–151° C.
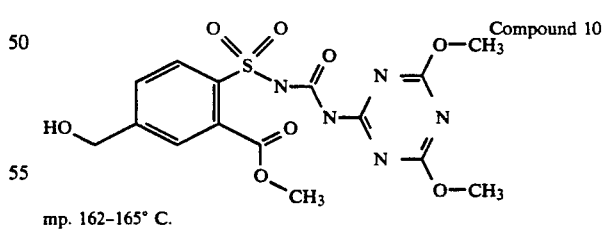
Compound 10
mp. 162–165° C.
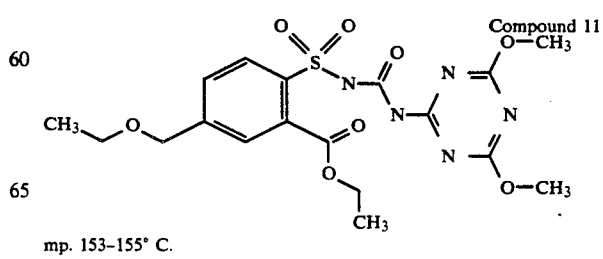
Compound 11
mp. 153–155° C.

-continued
COMPOUNDS
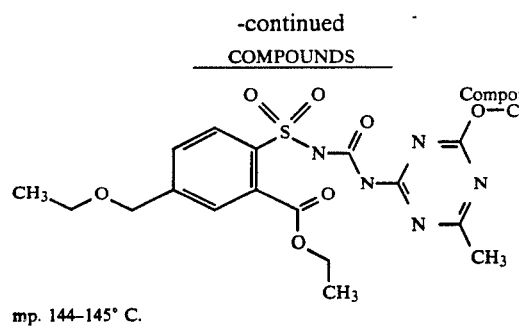
Compound 12
mp. 144–145° C.
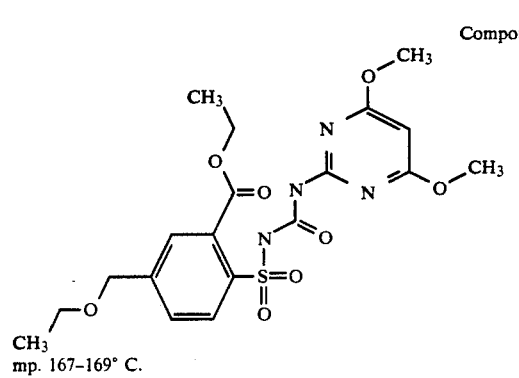
Compound 13
mp. 167–169° C.
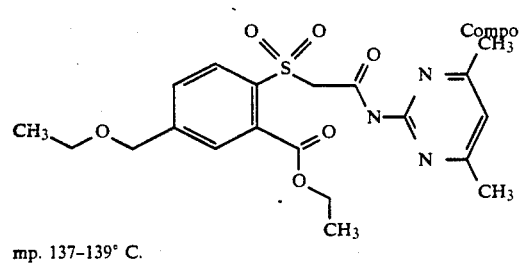
Compound 14
mp. 137–139° C.
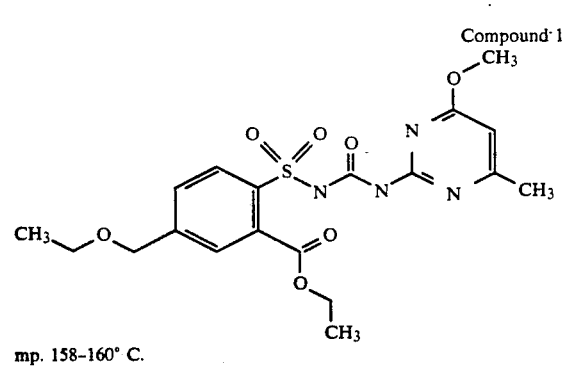
Compound 15
mp. 158–160° C.
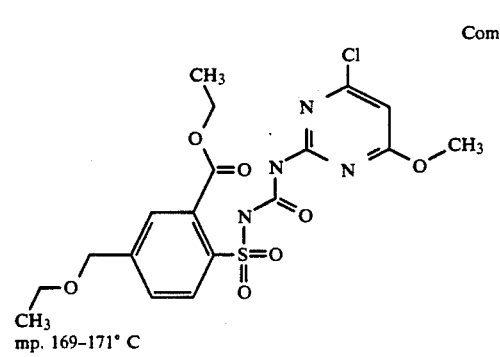
Compound 16
mp. 169–171° C
-continued
COMPOUNDS
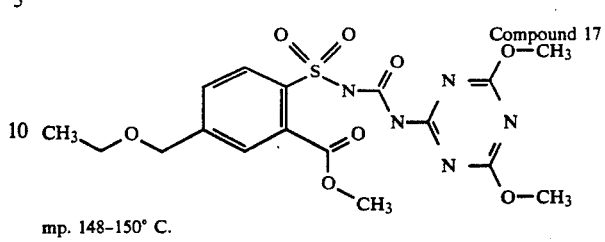
Compound 17
mp. 148–150° C.
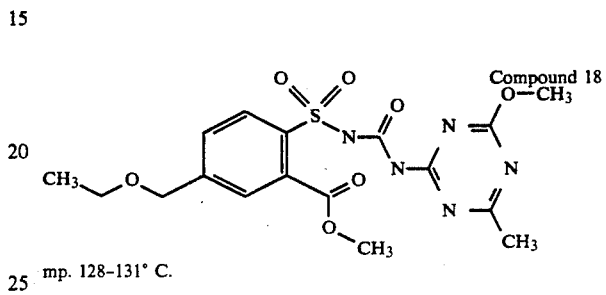
Compound 18
mp. 128–131° C.
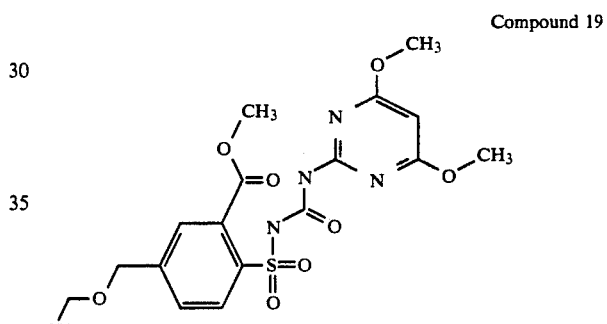
Compound 19
mp. 157–159° C.
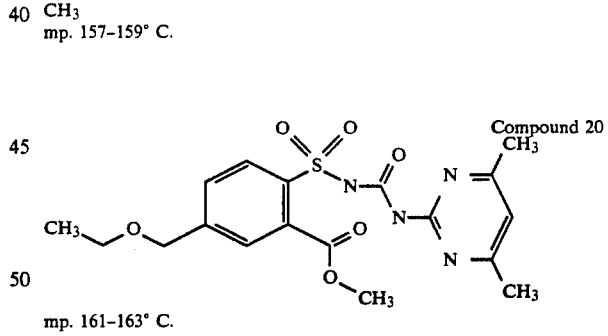
Compound 20
mp. 161–163° C.
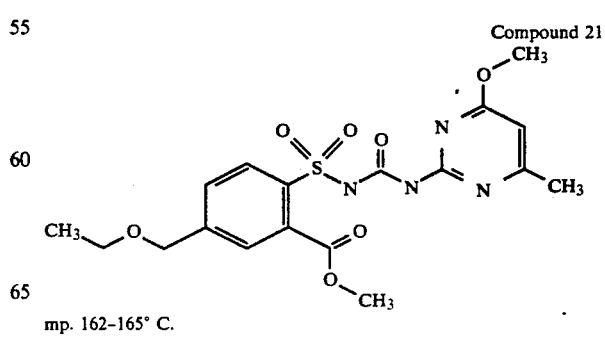
Compound 21
mp. 162–165° C.

-continued
COMPOUNDS
Compound 22
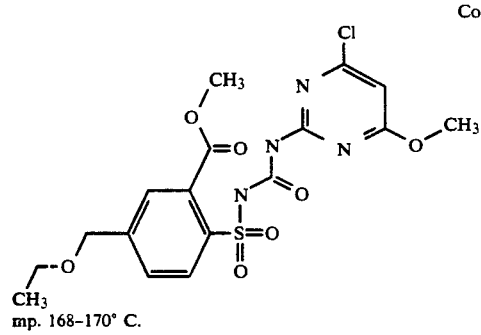
mp. 168–170° C.
Compound 23
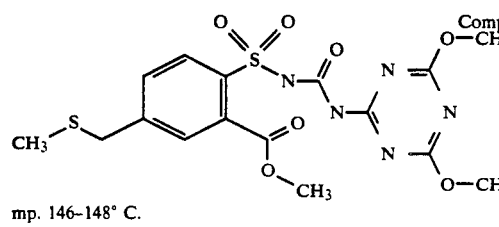
mp. 146–148° C.
Compound 24
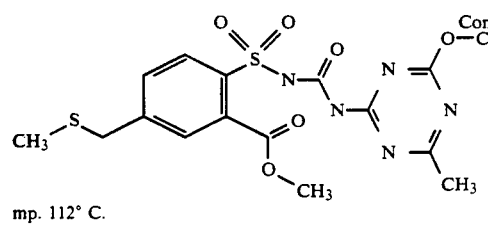
mp. 112° C.
Compound 25
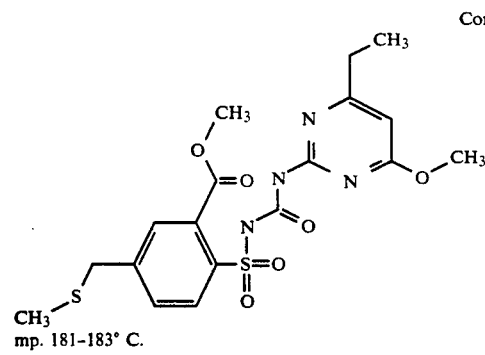
mp. 181–183° C.
Compound 26
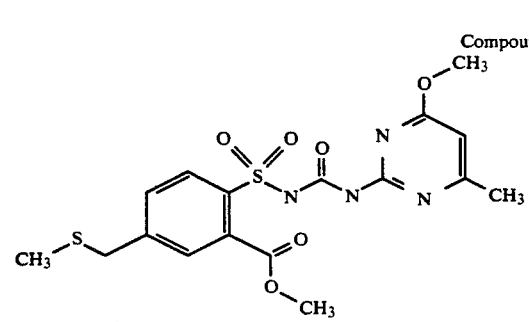
mp. 186–189° C.
-continued
COMPOUNDS
Compound 27
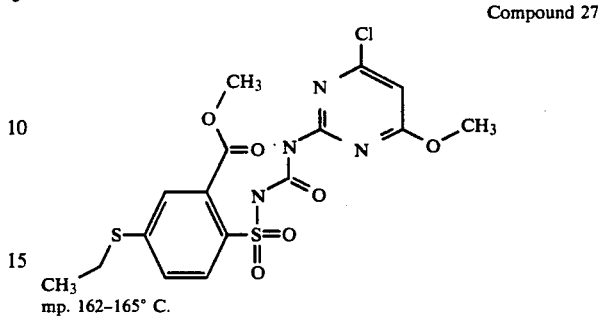
mp. 162–165° C.
Compound 28
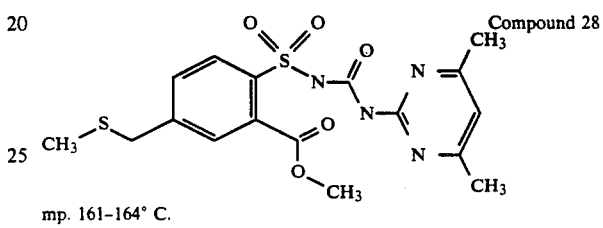
mp. 161–164° C.
Compound 29
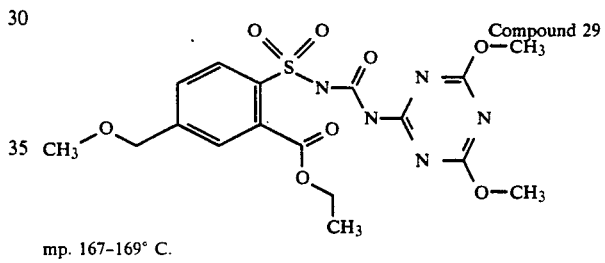
mp. 167–169° C.
Compound 30
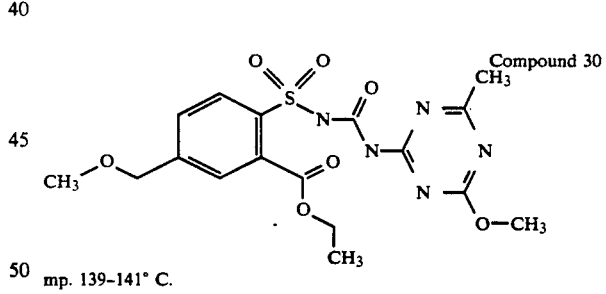
mp. 139–141° C.
Compound 31
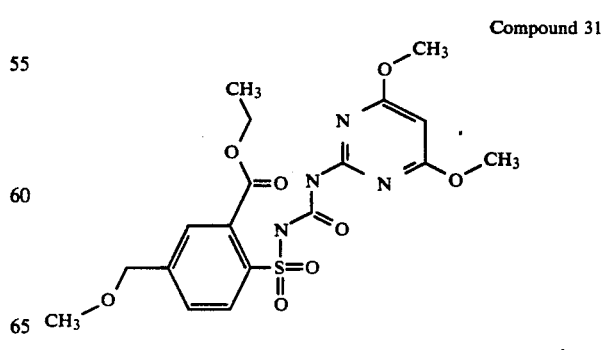
mp. 147–150° C.

-continued

COMPOUNDS

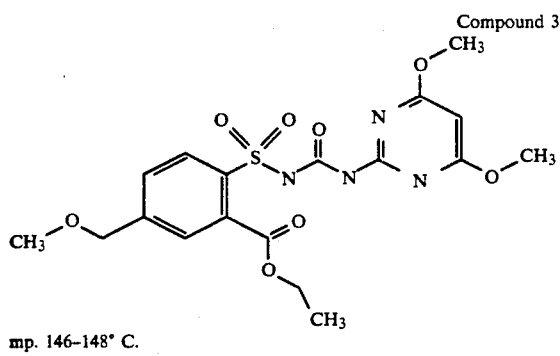

Compound 32 mp. 146-148° C.

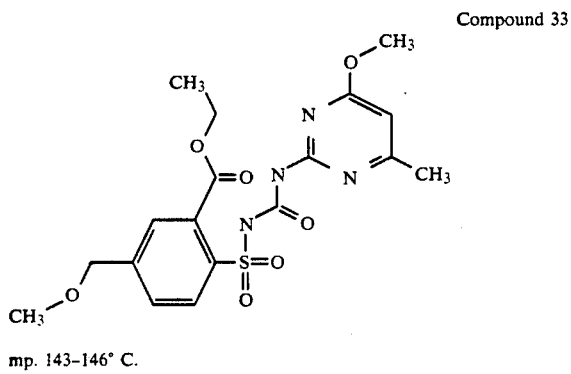

Compound 33 mp. 143-146° C.

-continued
COMPOUNDS

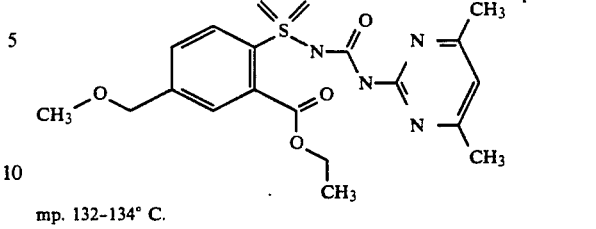

Compound 34 mp. 132-134° C.

TEST A

Seeds of barley (*Hordeum vulgare*), barnyardgrass (*Echinochloa crus-galli*), cheatgrass (*Bromus secalinus*), cocklebur (*Xanthium pensylvanicum*), corn (*Zea mays*), cotton (*Gossypium hirsutum*), crabgrass (Digitaria spp.), giant foxtail (*Setaria faberi*), morningglory (Ipomoea spp.), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately sixteen days, after which all species were compared to controls and visually evaluated. The ratings, summarized in Table A, are based on a scale of 0 to 10 where 0 is no effect and 10 is complete control. A dash (-) response means no test result. The accompanying descriptive symbols have the following meanings:
C=chlorosis/necrosis;
E=inhibition of emergence;
G=growth retardation;
H=formative effect; and
U=unusual pigmentation.

TABLE A

POSTEMERGENCE

| RATE (g/ha) | Cmpd 1 | | Cmpd 2 | | Cmpd 3 | | Cmpd 4 | | Cmpd 5 | | Cmpd 6 | | Cmpd 7 | | Cmpd 8 | | Cmpd 9 | | Cmpd 10 | | Cmpd 11 | | Cmpd 12 | |
|---|---|---|---|---|---|---|---|---|---|---|---|---|---|---|---|---|---|---|---|---|---|---|---|---|
| | 50 | 10 | 50 | 10 | 50 | 10 | 50 | 10 | 50 | 10 | 50 | 10 | 50 | 10 | 50 | 10 | 50 | 10 | 50 | 10 | 50 | 10 | 50 | 10 |
| Barley | 9G | 6G | 8G | 0 | 9G | 0 | 8G | 3C,9G | 9G | 2C,7G | 2C,8G | 2C,5G | 2C,9G | 3C,7G | 4C,8G | 3C,5G | 3C,5G | 4G | 0 | 0 | 9G | 2C,7G | 9G | 3C,8G |
| Barnyardgrass | 3C,8H | 4G | 3C,9H | 0 | 9G | 0 | 3C,9H | 3C,7H | 3C,8H | 3C,8H | 3C,5H | 1H | 9G | 3C,9H | 3C,5H | 3C,7G | 3C,7G | 3H | 0 | 0 | 3C,7G | 3G | 2C,5G | 0 |
| Cheatgrass | 5C,9G | 7G | 5C,5G | 3G | 5G | 0 | 6G | 2C,9G | 2G | 5G | 5G | 0 | 0 | 2G | 2G | 0 | 0 | 0 | 0 | 0 | 2C,4G | 0 | 2C,4H | 0 |
| Cocklebur | 2C,6G | 1C | 2C,3H | 0 | 10C | 0 | 4C,9G | 2C,8G | 3C,8H | 2C,2H | 2C,2H | 1C | 4C,9G | 4C,9G | 3C,9G | 2C,7G | 2C,9H | 2C,5G | 0 | 0 | 0 | 0 | 2C | 0 |
| Corn | 3C,8G | 3C,6H | 3C,9G | 0 | 10C | 0 | 4C,9G | 3C,9G | 3C,9G | 3C,6G | 3C,6G | 3C,8H | 3C,9G | 3C,9G | 9H | 2C,5G | 3C,9H | 2C,4G | 0 | 0 | 4C,9G | 2C,4G | 3C,9H | 2C,5G |
| Cotton | 3C,7H | 0 | 5U,9G | 2C,3G | 3U,9G | 0 | 4C,9G | 2C,8H | 9H | 3C,8H | 3C,6G | 3C,8H | 4C,9H | 4C,9H | 3C,6H | 2C,7G | 9H | 2C,4G | 0 | 0 | 4C,9G | 0 | 3C,5G | 0 |
| Crabgrass | 3C,8G | 0 | 3C,8G | 0 | 9C | 0 | 2C,6G | 0 | 0 | 0 | 3C,7H | 0 | 5G | 0 | 3C,6H | 2C,4G | 9C | 2G | 0 | 0 | 0 | 0 | 0 | 0 |
| Giant foxtail | 3C,9G | 2G | 3G | 0 | 4C,9G | 0 | 2C,9G | 2G | 3C,7G | 0 | 2C,4G | 0 | 3C,7G | 3C,9G | 3C,4G | 2C,4G | 7G | 2G | 0 | 0 | 1C | 0 | 2G | 0 |
| Morningglory | 4C,8H | 2C,2H | 4C,8H | 0 | 3C,9G | 0 | 4C,9G | 2C,4G | 2C,7G | 0 | 3C,8H | 2C,4H | 5C,9G | 3C,7H | 2C,4G | 2C,4G | 4C,9G | 2G | 0 | 0 | 1C | 0 | 1C | 2G |
| Nutsedge | 5G | 4G | 5G | 0 | 10C | 0 | 5G | — | 4G | 0 | 3C,6H | 2G | 5H | 3C,8G | 5C,9G | 0 | 5C,9G | 0 | 0 | 0 | 1C,3H | 0 | 0 | 0 |
| Rice | 9C | 4C,9G | 5C,9G | 7G | 9C | 0 | 5C,9G | 5G | 5C,9G | 5C,9G | 5C,9G | 3C,8G | 5C,9G | 5C,9G | 4C,9G | 4C,9G | 4C,9G | 8G | 4C,9G | 5G | 4C,9G | 3C,8G | 5C,9G | 8G |
| Sorghum | 4C,9G | 5G | 4C,9G | 0 | 3C,8G | 3G | 5G | 2G | 4C,4G | 2C,4G | 3C,6G | 3C,6G | 3C,7G | 4C,9G | 3C,6G | 2G | 4C,9G | 2G | 2G | 0 | 4C,9G | 3C,5G | 4C,9G | 1C,6G |
| Soybean | 2C,2G | 1C,2G | 1C | 0 | 2C,7G | 0 | 3C,1H | 2C,5H | 2H | 3C,4H | 3C,4H | 1C | 3C,8G | 5H | 3C,4H | 0 | 1H | 0 | 0 | 0 | 1C,1H | 0 | 1C,1H | 0 |
| Sugar beet | 0 | 0 | 1C,2G | 0 | 9C | 0 | 5C,5H | 0 | 0 | 1H | 2C,5G | 0 | 2H | 4C,9G | 0 | 0 | 0 | 0 | 0 | 0 | 4C,7G | 1H | 4C,7G | 0 |
| Velvetleaf | 0 | 0 | 1C,1H | 0 | 2C,6G | 0 | 4G | 0 | 1H | 0 | 0 | 0 | 4C,9G | 3G | 4C,9G | 2C,6G | 4C,9G | 8G | 5G | 0 | 0 | 1H | 0 | 0 |
| Wheat | 4G | 0 | 4G | 0 | 9G | 0 | 8G | 0 | 4G | 0 | 2C,5G | 0 | 7H | 0 | 2C,6G | 3G | 2C,5G | 2G | 0 | 0 | 5G | 0 | 5G | 0 |
| Wild oat | 0 | 0 | 0 | 0 | 4G | 0 | 2G | 0 | 0 | 0 | 2G | 0 | 1C | 0 | 1C | 0 | 2G | 0 | 0 | 0 | 0 | 0 | 0 | 0 |

| RATE (g/ha) | Cmpd 13 | | Cmpd 14 | | Cmpd 15 | | Cmpd 16 | | Cmpd 17 | | Cmpd 18 | | Cmpd 19 | | Cmpd 20 | | Cmpd 21 | | Cmpd 22 | | Cmpd 23 | |
|---|---|---|---|---|---|---|---|---|---|---|---|---|---|---|---|---|---|---|---|---|---|---|
| | 50 | 10 | 50 | 10 | 50 | 10 | 50 | 10 | 50 | 10 | 50 | 10 | 50 | 10 | 50 | 10 | 50 | 10 | 50 | 10 | 50 | 10 |
| Barley | 9G | 3C,8H | 3C,7G | 2C,3G | 3C,7G | 0 | 3C,5G | 2H | 3C,9G | 2C,7G | 3C,9G | 3C,7G | 2C,9G | 3C,7G | 4C,8G | 3C,7G | 2C,9G | 3C,7G | 3C,7H | 3C,7H | 0 | 0 |
| Barnyardgrass | 4C,9H | 9G | 4C,8H | 0 | 3C,3G | 0 | 3C,9H | 0 | 4C,8G | 2C,4G | 3C,6G | 4H | 9H | 3G | 3C,5H | 3G | 4C,9H | 3C,7G | 3C,7H | 3C,7H | 0 | 0 |
| Cheatgrass | 3G | 0 | 4C,9G | 0 | 3G | 0 | 6G | 5G | 3G | 5G | 3G | 3H | 2C,7G | 0 | 2G | 0 | 2C,5G | 4C,9G | 2G | 0 | 0 | 0 |
| Cocklebur | 9C | 0 | 4C,9G | 0 | 4C,9G | 3G | 3C,8H | 0 | 1H | 0 | 2C,5G | 3C,6H | 5C,9G | 3C,7G | 4C,9G | 0 | 4C,9G | 3C,9H | 3C,8H | 0 | 1H | 0 |
| Corn | 5C,9G | 3C,9G | 5U,9G | 1C | 4C,9G | 3G | 4C,9G | 2H | 4C,9G | 2C,4G | 4C,9G | 2C,6H | 5C,9G | 3C,7G | 5C,9G | 3C,7G | 4C,9G | 3C,9H | 3C,6G | 2G | 2H | 1H |
| Cotton | 2C,9G | 2C,8G | 3C,8G | 0 | 4C,9G | 3C,8G | 4C,9G | 0 | 0 | 0 | 4C,8G | 2C,6H | 3C,9H | 2G | 3C,8G | 0 | 4C,8G | 3C,6G | 3C,8H | 2G | 3C,7H | 3G |
| Crabgrass | 2C,9G | 0 | 2G | 0 | 3C,7G | 0 | 0 | 0 | 0 | 0 | 0 | 0 | 3C,7G | 0 | 3C,8G | 0 | 2C,4G | 0 | 3C,6G | 2G | 0 | 0 |
| Giant foxtail | 2C,2G | 0 | 1H | 0 | 0 | 0 | 0 | 0 | 2G | 0 | 2G | 0 | 3C,6G | 2H | 4C,9G | 0 | 3C,5G | 3C,5G | 3C,5G | 2G | 4C,8H | 2C,4H |
| Morningglory | 10C | 2C,2H | 1C | 0 | 2C,5G | 1C | — | 0 | 2G | 0 | 4C,9G | 0 | 2C,7G | 0 | 4C,8G | 3C,7G | 2C,7H | 3C,7H | 3C,6G | 2H | 5G | 0 |
| Nutsedge | 2C,8G | 0 | 3C,7G | 3G | 3G | 7G | 0 | 0 | 0 | 0 | 0 | 0 | 2C,7G | 0 | 3C,8G | 0 | 3C,8G | 2C,6G | 5C,9G | 4G | 0 | 0 |
| Rice | 5C,9G | 4C,9G | 3C,7G | 1C | 4C,9G | 3C,8G | 4C,9G | 5G | 5C,9G | 5C,9G | 5C,9G | 5G | 9G | 3C,9G | 4C,8G | 3C,7G | 5C,9G | 5C,9G | 5C,9G | 3C,8G | 5C,9G | 8G |
| Sorghum | 3C,9G | 9G | 3C,8G | 2G | 4C,9G | 3C,8G | 4C,9G | 2G | 4C,9G | 4C,9G | 4C,9G | 3C,8H | 4C,9G | 3C,7G | 4C,8G | 3C,6H | 4C,9G | 3C,8G | 3C,9G | 3C,8G | 4C,9G | 1C,6G |
| Soybean | 3C,8G | 3C,7H | 2C,3H | 0 | 2C,3H | 1H | 2H | 0 | 2C,5H | 3C,6H | 3C,8H | 3C,4H | 4C,7G | 1H | 3C,6H | 1H | 5C,9G | 4H | 2H | 0 | 1C,1H | 0 |
| Sugar beet | 1C | 0 | 1H | 0 | 2H | 0 | 0 | 3G | 10C | 0 | 4C,9G | 0 | 4C,9G | 4C,9G | 7H | 0 | 3C,8H | 3C,5H | 4C,9G | 4C,9G | 4C,7G | 0 |
| Velvetleaf | 4C,8G | 0 | 4G | 0 | 0 | 0 | 0 | 0 | 2C,6G | 0 | 4C,8G | 0 | 2C,6G | 1H | 2C,8G | 1C | 3C,7G | 2C,2G | 2C,5G | 1H | 1H | 0 |
| Wheat | 5G | 0 | 0 | 0 | 8G | 5G | 0 | 0 | 1C | 0 | 5G | 2G | 9G | 3G | 9G | 6G | 2C,5G | 3G | 4G | 5G | 5G | 0 |
| Wild oat | 2G | 0 | 0 | 0 | 2C,3G | 0 | 0 | 0 | 0 | 0 | 2G | 3H | 1C | 0 | 3C,4H | 3C,3G | 0 | 0 | 0 | 0 | 0 | 0 |

| RATE (g/ha) | Cmpd 24 | | Cmpd 25 | | Cmpd 26 | | Cmpd 27 | | Cmpd 28 | | Cmpd 29 | | Cmpd 30 | | Cmpd 31 | | Cmpd 32 | | Cmpd 33 | | Cmpd 34 | |
|---|---|---|---|---|---|---|---|---|---|---|---|---|---|---|---|---|---|---|---|---|---|---|
| | 50 | 10 | 50 | 10 | 50 | 10 | 50 | 10 | 50 | 10 | 50 | 10 | 50 | 10 | 50 | 10 | 50 | 10 | 50 | 10 | 50 | 10 |
| Barley | 0 | 0 | 3C,7G | 0 | 0 | 0 | 3G | 0 | 0 | 0 | 8G | 7G | 6G | 0 | 9G | 8G | 4G | 4G | 4G | 0 | 0 | 0 |
| Barnyardgrass | 0 | 0 | 4C,8H | 2C,5G | 3C,6G | 2G | 0 | 0 | 2G | 0 | 2C,4H | 4H | 2H | 0 | 10C | 3C,9H | 3H | 4C,8H | 4C,9H | 2C,5H | 0 | 0 |
| Cheatgrass | 2C,2H | 1H | 2C,5G | 0 | 3C,6H | 0 | 0 | 0 | 5G | 0 | 2H | 3H | 0 | 0 | 4G | 5G | 3G | 5G | 3G | 2C,5H | 0 | 0 |
| Cocklebur | 0 | 0 | 4C,9G | 4C,9G | 3C,6H | 3G | 2C,5G | 0 | 0 | 0 | 3U,9G | 2C,6H | 3C,6H | 3C,6H | 10C | 3C,9H | 3C,9H | 4C,8H | 4C,8H | 1C,2G | 0 | 0 |
| Corn | 2C,2G | 0 | 3C,8G | 3C,8G | 3C,7G | 3G | 3C,5H | 0 | 2C,3G | 0 | 5G | 3C,9G | 0 | 0 | 10C | 8H | 3C,9H | 2C,3G | 2C,3G | 2C,2G | 0 | 0 |
| Cotton | 0 | 0 | 3C,7G | 2C,7G | 3C,7G | 2C,3H | 7H | 0 | 3C,5G | 0 | 3G | 4G | 0 | 0 | 9G | 6G | 8H | 2G | 2G | 0 | 0 | 0 |
| Crabgrass | 2C,5G | 0 | 2G | 0 | 3C,5G | 0 | 0 | 0 | 0 | 0 | 4G | 2G | 0 | 0 | 5G | 0 | 0 | 0 | 0 | 0 | 0 | 0 |
| Giant foxtail | 0 | 0 | 3C,8G | 0 | 3C,8G | 0 | 0 | 0 | 2C,3G | 0 | 2G | 0 | 0 | 0 | 3C,8G | 2G | 0 | 0 | 0 | 0 | 3G | 0 |
| Morningglory | 4C,8G | 2C,2H | 5C,9G | 1C,2H | 3C,8H | 0 | 2C,2H | 0 | 3C,5G | 0 | 3H | 0 | 0 | 0 | 3C,4H | 1C,1H | 0 | 0 | 0 | 0 | 0 | 0 |

TABLE A-continued

|  | Cmpd 1 | | Cmpd 2 | | Cmpd 3 | | Cmpd 4 | | Cmpd 5 | | Cmpd 6 | | Cmpd 7 | | Cmpd 8 | | Cmpd 9 | | Cmpd 10 | | Cmpd 11 | | Cmpd 12 | |
|---|---|---|---|---|---|---|---|---|---|---|---|---|---|---|---|---|---|---|---|---|---|---|---|---|
| RATE (g/ha) | 50 | 10 | 50 | 10 | 50 | 10 | 50 | 10 | 50 | 10 | 50 | 10 | 50 | 10 | 50 | 10 | 50 | 10 | 50 | 10 | 50 | 10 | 50 | 10 |
| Nutsedge | 8G | 0 | — | 0 | 3C,6G | 0 | 0 | 0 | 0 | 0 | 2C,7G | 0 | 3C,9G | 0 | 5C,9G | 0 | 2C,5G | 0 | 0 | 0 | 0 | 0 | 0 | 0 |
| Rice | 3C,7G | 1C | 9C | 0 | 3C,8G | 0 | 9C | 0 | 7G | 2G | 0 | 0 | 9C | 7G | 4C,8G | 8G | 4C,8G | 8G | 0 | 7G | 2C,5G | 3G |
| Sorghum | 3G | 0 | 0 | 0 | 3C,7G | 0 | 0 | 0 | 3C,7H | 2G | 0 | 0 | 9C | 5G | 3C,9G | 9G | 9G | 6G | 0 | 0 | 2G | 5G | 0 |
| Soybean | 2C,6H | 1C,2H | 3C,9G | 0 | 3C,8G | 2H | 3C,8G | 0 | 2H | 4G | 5C,9G | 7G | 8G | 0 | 3C,8G | 6H | 4H | 2H | 0 | 0 | 0 | 0 | 0 |
| Sugar beet | 5C,9G | 3C,6H | 3C,8G | 0 | 5C,9G | 3C,6G | 2H | 0 | 3C,2H | 1H | 3C,8G | 1C,1H | 1C | 0 | 4C,8G | 0 | 6H | 0 | 0 | 0 | 0 | 4G | 0 |
| Velvetleaf | 3C,7G | 2C | 9C | 0 | 5G | 0 | 7G | 0 | 0 | 0 | 0 | 0 | 4C,9G | 0 | 2G | 0 | 0 | 0 | 0 | 2G | 0 | 0 | 0 |
| Wheat | 0 | 0 | 3C,7G | 0 | 2G | 0 | 3G | 0 | 3C,5H | 0 | 3C,5H | 0 | 5G | 4C,9G | 8G | 7G | 5G | 2G | 4G | 0 |
| Wild oat | 0 | 0 | 6G | 0 | 0 | 0 | 2G | 0 | 0 | 0 | 0 | 0 | 2C,4G | 0 | 2C,3G | 2G | 0 | 0 | 0 | 0 | 0 | 0 |

PREEMERGENCE

|  | Cmpd 13 | | Cmpd 14 | | Cmpd 15 | | Cmpd 16 | | Cmpd 17 | | Cmpd 18 | | Cmpd 19 | | Cmpd 20 | | Cmpd 21 | | Cmpd 22 | | Cmpd 23 | |
|---|---|---|---|---|---|---|---|---|---|---|---|---|---|---|---|---|---|---|---|---|---|---|---|---|
| RATE (g/ha) | 50 | 10 | 50 | 10 | 50 | 10 | 50 | 10 | 50 | 10 | 50 | 10 | 50 | 10 | 50 | 10 | 50 | 10 | 50 | 10 | 50 | 10 |
| Barley | 3C,8G | 0 | 0 | 0 | 2C,8G | 5G | 3C,8G | 3G | 2C,5G | 2C,7G | 3C,6G | 2C,7G | 6G | 2C,2G | 0 | 5G | 0 | 2C,6G | 3C,8G | 6G |
| Barnyardgrass | 3C,9H | 0 | 0 | 0 | 3C,7G | 1C | 3C,6G | 1C | 0 | 0 | 2G | 0 | 3C,8G | 0 | 0 | 0 | 3C,5G | 0 | 4C,9H | 3C,7G | 1C | 0 |
| Cheatgrass | 7G | 3G | 0 | 0 | 5G | 2C | 0 | 0 | 2G | 0 | 5G | 4G | 7G | 3G | 0 | 0 | 8G | 2C | 5G | 3G | 3G | 3G |
| Cocklebur | 8H | 2C,7H | 4G | 2G | 2C,5G | 0 | 3C,3G | 0 | 2C,2G | 0 | 5H | 0 | 3C,5H | 5H | 0 | 0 | 3C,5H | 2C | 5G | 1C | 1C | 0 |
| Corn | 3C,9G | 3C,6G | 2G | 0 | 3C,7G | 3C,4G | 3C,5G | 2C,2G | 2C,2G | 0 | 4C,8H | 2C,3G | 3C,3G | 5G | 3G | 0 | 4C,9G | 3C,5G | 4C,9H | 3C,8H | 3C,3G | 2C |
| Cotton | 8G | 3H | 0 | 0 | 0 | 0 | 2G | 0 | 4G | 0 | 7G | 0 | 7G | 2G | 3H | 0 | 3H | 0 | 1H | 0 | 1H | 2H |
| Crabgrass | 5G | 0 | 2G | 0 | 2C,6G | 3G | 2G | 0 | 0 | 0 | 2G | 0 | 2G | 4G | 0 | 0 | 5G | 0 | 5G | 3C,5G | 3C,3G | 0 |
| Giant foxtail | 5G | 0 | 3G | 0 | 1C | 0 | 2C,5G | 0 | 2G | 0 | 6G | 0 | 5G | 1C | 0 | 0 | 3C,5G | 3C,5G | 3C,5G | 5G | 3C,8H | 0 |
| Morningglory | 6H | 2G | 4G | 0 | 2C | 0 | 2G | 0 | 2C | 0 | 8G | 0 | 5G | 2G | 0 | 0 | 2C,7G | 7H | 7H | 0 | 3H | 0 |
| Nutsedge | 3C,5G | 0 | 0 | 0 | 3C,9G | 0 | 0 | 0 | 0 | 0 | 2C,5G | 0 | 5G | 4G | 0 | 0 | 4G | 0 | 9H | 4G | 4G | 2G |
| Rice | 9H | 7G | 4G | 0 | 10H | 0 | 5G | 2G | 8H | 0 | 7G | 0 | 9H | 7G | 0 | 0 | 4C,8G | 4C,9H | 4C,9H | 5G | 0 | 2G |
| Sorghum | 3C,6G | 3C,6G | 2C,5G | 0 | 3C,9H | 7H | 3C,7G | 4G | 3C,7H | 0 | 2C,9G | 3G | 4C,9G | 2C,3G | 0 | 0 | 4C,7H | 3C,3G | 3C,3H | 3C,6G | 2C,2H | 2C |
| Soybean | 3C,6H | 2G | 2G | 0 | 2C,4G | 2C,4G | 3C,4H | 0 | 5G | 3C,3G | 3C,7H | 2C,5G | 2C,2G | 6G | 0 | 0 | 3C,3H | 3C,3H | 4C,9H | 1C,1H | 0 |
| Sugar beet | 0 | 0 | 0 | 0 | 4C,8H | 2G | 3C,4H | 2H | 2G | 0 | 6G | 0 | 0 | 0 | 3H | 0 | 5H | 9G | 9G | 5G | 6G | 0 |
| Velvetleaf | 2C,5H | 3H | 0 | 0 | 0 | 0 | 2C,6H | 1H | 5G | 3G | 4H | 0 | 2H | 0 | 0 | 0 | 3H | 0 | 4C,9H | 2H | 0 |
| Wheat | 7G | 6G | 0 | 0 | 2C,6G | 3G | 8G | 6G | 8G | 4G | 7G | 7G | 7G | 2C,3G | 0 | 0 | 8G | 5G | 6G | 5G | 5G | 2G |
| Wild oat | 2C,3G | 2G | 0 | 0 | 9G | 6G | 2C,7G | 3G | 3G | 0 | 3C,6G | 2C,3G | 3C,6G | 2C,3G | 0 | 0 | 3C,6G | 2C,4G | 2C,2G | 1C | 2G | 0 |

|  | Cmpd 24 | | Cmpd 25 | | Cmpd 26 | | Cmpd 27 | | Cmpd 28 | | Cmpd 29 | | Cmpd 30 | | Cmpd 31 | | Cmpd 32 | | Cmpd 33 | | Cmpd 34 | |
|---|---|---|---|---|---|---|---|---|---|---|---|---|---|---|---|---|---|---|---|---|---|---|---|---|
| RATE (g/ha) | 50 | 10 | 50 | 10 | 50 | 10 | 50 | 10 | 50 | 10 | 50 | 10 | 50 | 10 | 50 | 10 | 50 | 10 | 50 | 10 | 50 | 10 |

TABLE A-continued

| | C1 | C2 | C3 | C4 | C5 | C6 | C7 | C8 | C9 | C10 | C11 | C12 | C13 | C14 | C15 | C16 | C17 | C18 | C19 |
|---|---|---|---|---|---|---|---|---|---|---|---|---|---|---|---|---|---|---|---|
| Barley | 0 | 0 | 0 | 0 | 0 | 0 | 0 | 0 | 0 | 0 | 0 | 8G | 0 | 0 | 0 | 7G | 0 | 0 | 0 |
| Barnyardgrass | 0 | 0 | 0 | 0 | 0 | 0 | 0 | 0 | 0 | 0 | 0 | 3C,9H | 2C,6H | 7G | 0 | 5H | 0 | 0 | 0 |
| Cheatgrass | 0 | 0 | 2G | 0 | 0 | 0 | 0 | 0 | 0 | 0 | 0 | 6G | 2G | 3C,6H | 0 | 0 | 0 | 0 | 0 |
| Cocklebur | 0 | 0 | 2C,4G | 0 | 2C,2G | 0 | 2G | 0 | 0 | 2C | 2H | 9H | 3C,4H | 2G | 1C | 1C,2G | 0 | 2G | 0 |
| Corn | 2G | 0 | 3G | 0 | 2G | 0 | 0 | 0 | 0 | 1C | 3C,6G | 3C,9G | 2C,4G | 3C,3G | 2C | 0 | 0 | 0 | 0 |
| Cotton | 4G | 0 | 4G | 0 | 0 | 0 | 0 | 0 | 0 | 0 | 0 | 5G | 0 | 4C,6G | 0 | 0 | 0 | 0 | 0 |
| Crabgrass | 0 | 0 | 3G | 0 | 0 | 0 | 0 | 0 | 0 | 0 | 0 | 2C,3H | 0 | 0 | 0 | 0 | 0 | 0 | 0 |
| Giant foxtail | 0 | 0 | 0 | 0 | 0 | 0 | 0 | 0 | 0 | 0 | 0 | 6H | 2H | 0 | 0 | 0 | 0 | 3G | 0 |
| Morningglory | 2H | 0 | 1C | 0 | 0 | 0 | 0 | 0 | 0 | 0 | 0 | 2C,6H | 2C,2H | 2C,2H | 0 | 0 | 0 | 0 | 0 |
| Nutsedge | 0 | 0 | 0 | 0 | 0 | 0 | 0 | 0 | 0 | 0 | 0 | 2G | 0 | 0 | 0 | 0 | 0 | 0 | 0 |
| Rice | 4G | 0 | 4G | 0 | 2C,3G | 0 | 0 | 0 | 0 | 5H | 3G | 9H | 8H | 3C,6H | 0 | 8H | 0 | 0 | 0 |
| Sorghum | 2G | 0 | 3C,5G | 0 | 2G | 0 | 0 | 0 | 0 | 2C,4G | 2C,5G | 9H | 2G | 3C,6H | 0 | 3G | 0 | 2G | 0 |
| Soybean | 2C,2H | 2G | 2C,2H | 0 | 2C | 2G | 0 | 0 | 0 | 1H | 0 | 3C,3H | 1C | 2C | 0 | 0 | 0 | 1H | 0 |
| Sugar beet | 5G | 2G | 1H | 0 | 7G | 0 | 0 | 0 | 0 | 4G | 0 | 1C | 0 | 0 | 0 | 2G | 0 | 0 | 0 |
| Velvetleaf | 5G | 0 | 1H | 0 | 0 | 0 | 0 | 0 | 0 | 3G | 2G | 5H | 0 | 5G | 0 | 0 | 0 | 0 | 0 |
| Wheat | 0 | 0 | 0 | 0 | 0 | 0 | 0 | 0 | 0 | 0 | 0 | 5H | 0 | 2G | 0 | 0 | 0 | 0 | 0 |
| Wild oat | 0 | 0 | 0 | 0 | 0 | 0 | 0 | 0 | 0 | 0 | 0 | 2C,3G | 0 | 0 | 0 | 0 | 0 | 0 | 0 |

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria* spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (*Ipomoea* spp.), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. The ratings, summarized in Table B, are based on a scale of 0 to 100 where 0 is no effect and 100 is complete control. A dash (-) response means no test result.

TABLE B

POSTEMERGENCE

| RATE (g/ha) | Cmpd 3 62 | Cmpd 3 16 | Cmpd 3 4 | Cmpd 7 1 | Cmpd 7 250 | Cmpd 7 62 | Cmpd 7 16 | Cmpd 7 4 | Cmpd 13 500 | Cmpd 13 250 | Cmpd 13 125 | Cmpd 13 62 | Cmpd 19 250 | Cmpd 19 62 | Cmpd 19 16 | Cmpd 19 4 | Cmpd 31 250 | Cmpd 31 62 | Cmpd 31 16 | Cmpd 31 4 |
|---|---|---|---|---|---|---|---|---|---|---|---|---|---|---|---|---|---|---|---|---|
| Barley | 90 | 70 | 50 | 30 | 80 | 60 | 30 | 0 | 60 | 60 | 60 | 60 | 60 | 60 | 60 | 60 | 70 | 60 | 60 | 60 |
| Barnyardgrass | 90 | 80 | 70 | 50 | 100 | 90 | 80 | 70 | 100 | 100 | 95 | 90 | 100 | 95 | 90 | 80 | 100 | 90 | 85 | 80 |
| Blackgrass | 60 | 50 | 40 | 0 | 0 | 0 | 0 | 0 | 70 | 60 | 50 | 40 | 90 | 70 | 50 | 30 | 70 | 60 | 40 | 30 |
| Chickweed | 60 | 30 | 0 | 0 | 80 | 100 | 30 | 20 | 80 | 80 | 70 | 80 | 100 | 90 | 70 | 50 | 90 | 80 | 50 | 30 |
| Cocklebur | 90 | 70 | 50 | 30 | 100 | 100 | 90 | 40 | 100 | 100 | 90 | 70 | 100 | 80 | 60 | 50 | 90 | 70 | 60 | 30 |
| Corn | 70 | 70 | 30 | 0 | 100 | 95 | 100 | 60 | 100 | 100 | 100 | 80 | 100 | 70 | 70 | 40 | 80 | 80 | 70 | 70 |
| Cotton | 70 | 50 | 50 | 40 | 100 | 40 | 90 | 60 | 100 | 100 | 90 | 70 | 100 | 90 | 80 | 50 | 100 | 90 | 60 | 50 |
| Crabgrass | 30 | 0 | 0 | 0 | 45 | 20 | 20 | 0 | 70 | 60 | 30 | 80 | 60 | 30 | 0 | 0 | 70 | 50 | 30 | 40 |
| Downy brome | 80 | 50 | 30 | 0 | 50 | 100 | 90 | 40 | 70 | 60 | 40 | 40 | 70 | 50 | 40 | 30 | 50 | 50 | 40 | 0 |
| Giant foxtail | 90 | 80 | 70 | 0 | 100 | 80 | 70 | 40 | 90 | 90 | 60 | 60 | 80 | 100 | 100 | 70 | 80 | 70 | 30 | 0 |
| Green foxtail | 90 | 70 | 50 | 50 | 90 | 80 | 70 | 0 | 70 | 70 | 70 | 70 | 80 | 90 | 80 | 70 | 80 | 70 | 40 | 0 |
| Jimsonweed | 100 | 50 | 40 | 30 | — | 50 | 20 | 0 | 90 | 60 | 50 | 40 | 70 | 50 | 40 | 30 | 90 | 60 | 50 | 40 |
| Johnsongrass | 70 | 50 | 30 | 0 | 70 | 60 | 50 | 0 | 100 | 100 | 90 | 80 | 95 | 90 | 70 | 50 | 100 | 80 | 70 | 60 |
| Lambsquarters | 80 | 70 | 60 | 50 | 90 | 80 | 30 | 20 | 80 | 80 | 70 | 60 | 100 | 80 | 100 | 50 | 100 | 100 | 50 | 40 |
| Morningglory | 70 | 60 | 30 | 0 | 85 | 85 | 40 | 30 | 100 | 80 | 70 | 60 | 100 | 90 | 70 | 40 | 100 | 80 | 70 | 40 |
| Nutsedge | 70 | 50 | 30 | 0 | 75 | 50 | 50 | 50 | 50 | 50 | 50 | 50 | 70 | 60 | 30 | 0 | 90 | 70 | 50 | 40 |
| Rape | 100 | 100 | 100 | 70 | 100 | 100 | 100 | 80 | 100 | 100 | 100 | 100 | 100 | 100 | 100 | 100 | 100 | 100 | 100 | 90 |
| Rice | 90 | 70 | 50 | 30 | 100 | 100 | 85 | 90 | 80 | 90 | 80 | 60 | 90 | 90 | 80 | 70 | 90 | 80 | 70 | 60 |
| Sickepod | 60 | 30 | 30 | 0 | 40 | 40 | 95 | 0 | 60 | 40 | 20 | 0 | 80 | 60 | 30 | 0 | 70 | 30 | 0 | 0 |
| Soybean | 70 | 50 | 30 | 0 | 60 | 55 | 35 | 30 | 95 | 90 | 80 | 80 | 100 | 90 | 80 | 60 | 70 | 65 | 40 | 30 |
| Sugar beet | 60 | 30 | 0 | 0 | 40 | 35 | 40 | 0 | 90 | 70 | 50 | 30 | 100 | 90 | 90 | 60 | 70 | 60 | 40 | 30 |
| Teaweed | 90 | 70 | 60 | 50 | 85 | 60 | 30 | 30 | 70 | 70 | 85 | 80 | 90 | 80 | 70 | 50 | 95 | 90 | 70 | 40 |
| Velvetleaf | 100 | 80 | 70 | 30 | 100 | 100 | 40 | 50 | 100 | 100 | 100 | 100 | 100 | 100 | 100 | 100 | 95 | 90 | 70 | 60 |
| Wheat | 70 | 50 | 30 | 0 | 30 | 20 | 0 | 50 | 60 | 50 | 50 | 50 | 60 | 60 | 60 | 20 | 50 | 40 | 40 | 40 |
| Wild buckwheat | 90 | 60 | 30 | 50 | 100 | 50 | 50 | 30 | 95 | 90 | 80 | 70 | 95 | 90 | 80 | 60 | 100 | 75 | 70 | 50 |
| Wild oat | 70 | 50 | 0 | 0 | 0 | 0 | 0 | 0 | 60 | 50 | 40 | 30 | 60 | 40 | 40 | 30 | 70 | 50 | 30 | 0 |

PREEMERGENCE

| RATE (kg/ha) | Cmpd 3 62 | Cmpd 3 16 | Cmpd 3 4 | Cmpd 7 1 | Cmpd 7 250 | Cmpd 7 62 | Cmpd 7 16 | Cmpd 7 4 | Cmpd 13 500 | Cmpd 13 250 | Cmpd 13 125 | Cmpd 13 62 | Cmpd 19 250 | Cmpd 19 62 | Cmpd 19 16 | Cmpd 19 4 | Cmpd 31 250 | Cmpd 31 62 | Cmpd 31 16 | Cmpd 31 4 |
|---|---|---|---|---|---|---|---|---|---|---|---|---|---|---|---|---|---|---|---|---|
| Barley | 70 | 50 | 0 | 0 | 40 | 20 | 0 | 0 | 80 | 75 | 70 | 60 | 70 | 60 | 50 | 40 | 80 | 80 | 60 | 30 |
| Barnyardgrass | 100 | 90 | 60 | 30 | 95 | 90 | 40 | 0 | 100 | 100 | 90 | 85 | 100 | 90 | 60 | 30 | 100 | 100 | 70 | 30 |
| Blackgrass | 100 | 80 | 50 | 30 | 50 | 30 | 0 | 0 | 90 | 80 | 70 | 60 | 90 | 70 | 70 | 50 | 90 | 50 | 50 | 30 |
| Chickweed | 90 | 80 | 70 | 50 | 30 | 40 | 30 | 30 | 90 | 80 | 70 | 80 | 95 | 80 | 70 | 60 | 80 | 80 | 50 | 30 |
| Cocklebur | 90 | 70 | 70 | 50 | 60 | 80 | 30 | 0 | 100 | 90 | 85 | 80 | 100 | 80 | 75 | 70 | 100 | 90 | 50 | 0 |
| Corn | 80 | 60 | 50 | 30 | 80 | 40 | 0 | 0 | 95 | 90 | 85 | 75 | 100 | 70 | 30 | 0 | 100 | 80 | 70 | 0 |
| Cotton | 90 | 60 | 30 | 0 | 40 | 40 | 0 | 0 | 80 | 70 | 60 | 40 | 80 | 50 | 80 | 70 | 100 | 90 | 60 | 40 |
| Crabgrass | 100 | 90 | 70 | 30 | 80 | 50 | 0 | 0 | 100 | 85 | 80 | 75 | 100 | 90 | 80 | 0 | 100 | 70 | 70 | 50 |
| Downy brome | 80 | 50 | 30 | 60 | 0 | 0 | 0 | 0 | 80 | 70 | 70 | 60 | 80 | 50 | 30 | 0 | 80 | 50 | 60 | 40 |
| Giant foxtail | 100 | 100 | 80 | 70 | 80 | 30 | 20 | 40 | 90 | 80 | 80 | 70 | 100 | 80 | 80 | 50 | 100 | 70 | 70 | 0 |
| Green foxtail | 100 | 70 | 70 | 50 | 100 | 80 | 30 | 40 | 95 | 80 | 70 | 60 | 100 | 70 | 90 | 40 | 100 | 90 | 60 | 40 |
| Jimsonweed | 70 | 50 | 40 | 30 | 50 | 30 | 0 | 0 | 90 | 70 | 50 | 30 | 40 | 50 | 40 | 30 | 40 | 0 | 0 | 0 |
| Johnsongrass | 100 | 90 | 60 | 30 | 80 | 50 | 0 | 0 | 100 | 85 | 70 | 75 | 100 | 80 | 50 | 0 | 100 | 80 | 20 | 40 |
| Lambsquarters | 60 | 30 | 30 | 0 | 30 | 20 | 0 | 20 | 80 | 100 | 95 | 90 | 80 | 80 | 80 | 70 | 100 | 80 | 50 | 50 |
| Morningglory | 90 | 80 | 70 | 50 | 70 | 50 | 30 | 0 | 90 | 80 | 75 | 70 | 90 | 50 | 40 | 30 | 100 | 90 | 70 | 40 |
| Nutsedge | 70 | 50 | 30 | 0 | 70 | 40 | 30 | 20 | 90 | 80 | 70 | 60 | 80 | 70 | 50 | 70 | 90 | 60 | 60 | 0 |
| Rape | 90 | 80 | 70 | 50 | 0 | 0 | 30 | 0 | 90 | 80 | 100 | 75 | 80 | 80 | 40 | 30 | 60 | 90 | 100 | 50 |
| Rice | 90 | 80 | 70 | 50 | 90 | 100 | 100 | 40 | 100 | 85 | 95 | 100 | 100 | 90 | 90 | 60 | 100 | 90 | 70 | 30 |
| Sickepod | 70 | 60 | 50 | 40 | 40 | 30 | 0 | 0 | 40 | 30 | 20 | 0 | 90 | 40 | 0 | 30 | 100 | — | 80 | 80 |

TABLE B-continued

| | | | | | | | | | | | | | | | | | | | | |
|---|---|---|---|---|---|---|---|---|---|---|---|---|---|---|---|---|---|---|---|---|
| Soybean | 90 | 60 | 30 | 0 | 60 | 0 | 0 | 0 | 50 | 30 | 20 | 0 | 60 | 0 | 0 | 0 | 70 | 20 | 0 | 0 |
| Sugar beet | 30 | 20 | 0 | 0 | 0 | 0 | 0 | 0 | 90 | 80 | 70 | 60 | 90 | 60 | 50 | 80 | 80 | 50 | 30 | 20 |
| Teaweed | 80 | 70 | 50 | 30 | 50 | 30 | — | — | 90 | 80 | 75 | 70 | 95 | 70 | 80 | — | 100 | 100 | 100 | 50 |
| Velvetleaf | 80 | 70 | 60 | 30 | 80 | 50 | 0 | 0 | 100 | 100 | 90 | 40 | 90 | 40 | 30 | 0 | 80 | 0 | 0 | 0 |
| Wheat | 60 | 30 | 0 | 0 | 30 | 0 | 0 | 0 | 80 | 60 | 50 | 70 | 80 | 50 | 40 | 60 | 80 | 60 | 50 | 0 |
| Wild buckwheat | 70 | 50 | 30 | 0 | 70 | 50 | 30 | 0 | 90 | 80 | 75 | 80 | 90 | 75 | 70 | 100 | 100 | 100 | 90 | 30 |
| Wild oat | 70 | 50 | 30 | 0 | 0 | 0 | 0 | 0 | 70 | 50 | 50 | 30 | 70 | 30 | 0 | 50 | 60 | 50 | 30 | 30 |

TEST C

Seeds selected from blackgrass (*Alopecurus myosuroides*), catchweed bedstraw (*Galium aparine*), chickweed (*Stellaria media*), knotweed (*Polygonum aviculare*), lambsquarters (*Chenopodium album*), Persian speedwell (*Veronica persica*), scentless chamomille (*Matricaria inodora*), sugar beet (*Beta vulgaris*), viola (*Viola arvensis*), wheat (*Triticum aestivum*), wild buckwheat (*Polygonum convolvulus*), and wild oat (*Avena fatua*) were planted and treated preemergence with test chemicals dissolved in a non-phytotoxic solvent. Selected species from this list of crops and weeds were also treated with postemergence applications of test chemicals. Plants ranged in height from two to twenty cm (two to three leaf stage) for postemergence treatments. Treated plants and controls were maintained in a greenhouse for approximately 24 days, after which all species were compared to controls and visually evaluated. The ratings, summarized in Table C, are based on a scale of 0 to 100 where 0 is no effect and 100 is complete control. A dash (-) response means no test result.

TABLE C

| | Cmpd 1 | | | | | Cmpd 2 | | | | | Cmpd 3 | | | | |
|---|---|---|---|---|---|---|---|---|---|---|---|---|---|---|---|
| RATE (g/ha) | 125 | 64 | 32 | 16 | 8 | 125 | 64 | 32 | 16 | 8 | 64 | 32 | 16 | 8 | 4 |
| POSTEMERGENCE | | | | | | | | | | | | | | | |
| Blackgrass | 0 | 0 | 0 | 0 | 0 | 0 | 0 | 0 | 0 | 0 | 50 | 50 | 30 | 20 | 0 |
| Catchweed bedstraw | 0 | 0 | 0 | 0 | 0 | 0 | 0 | 0 | 0 | 0 | 100 | 100 | 100 | 50 | 0 |
| Chickweed | 0 | 0 | 0 | 0 | 0 | 0 | 0 | 0 | 0 | 0 | 80 | 80 | 20 | 0 | 0 |
| Knotweed | 0 | 0 | 0 | 0 | 0 | 0 | 0 | 0 | 0 | 0 | — | — | — | — | — |
| Lambsquarters | 0 | 0 | 0 | 0 | 0 | 0 | 0 | 0 | 0 | 0 | 0 | 0 | 0 | 0 | 0 |
| Persian speedwell | 0 | 0 | 0 | 0 | 0 | 0 | 0 | 0 | 0 | 0 | 0 | 0 | 0 | 0 | 0 |
| Scentless chamomille | 0 | 0 | 0 | 0 | 0 | 0 | 0 | 0 | 0 | 0 | 100 | 90 | 90 | 90 | 50 |
| Sugar beet | 0 | 0 | 0 | 0 | 0 | 0 | 0 | 0 | 0 | 0 | 20 | 10 | 0 | 0 | 0 |
| Viola | 0 | 0 | 0 | 0 | 0 | 0 | 0 | 0 | 0 | 0 | 90 | 50 | 50 | 50 | 50 |
| Wheat | 0 | 0 | 0 | 0 | 0 | 0 | 0 | 0 | 0 | 0 | 70 | 50 | 50 | 50 | 30 |
| Wild buckwheat | 0 | 0 | 0 | 0 | 0 | 0 | 0 | 0 | 0 | 0 | 90 | 90 | 75 | 50 | 30 |
| Wild oat | 20 | 0 | 0 | 0 | 0 | 0 | 0 | 0 | 0 | 0 | 50 | 50 | 50 | 30 | 0 |
| RATE (g/ha) | | | | | | | | | | | 64 | 32 | 16 | 8 | 4 |
| PREEMERGENCE | | | | | | | | | | | | | | | |
| Blackgrass | | | | | | | | | | | 90 | — | — | — | 50 |
| Catchweed bedstraw | | | | | | | | | | | 80 | — | — | — | 80 |
| Chickweed | | | | | | | | | | | 30 | — | — | — | 0 |
| Knotweed | | | | | | | | | | | 100 | — | — | — | 100 |
| Lambsquarters | | | | | | | | | | | — | — | — | — | — |
| Persian speedwell | | | | | | | | | | | 0 | — | — | — | 0 |
| Scentless chamomille | | | | | | | | | | | 90 | — | — | — | 80 |
| Sugar beet | | | | | | | | | | | 20 | — | — | — | 0 |
| Viola | | | | | | | | | | | 80 | — | — | — | 20 |
| Wheat | | | | | | | | | | | 80 | — | — | — | 20 |
| Wild buckwheat | | | | | | | | | | | 100 | — | — | — | 70 |
| Wild oat | | | | | | | | | | | 100 | — | — | — | 30 |

| | Cmpd 5 | | | | | Cmpd 7 | | | | |
|---|---|---|---|---|---|---|---|---|---|---|
| RATE (g/ha) | 125 | 64 | 32 | 16 | 8 | 250 | 125 | 64 | 32 | 16 |
| POSTEMERGENCE | | | | | | | | | | |
| Blackgrass | 30 | 30 | 30 | 30 | 0 | 40 | 30 | 0 | 0 | 0 |
| Catchweed bedstraw | 50 | 40 | 0 | 0 | 0 | 100 | 80 | 80 | 50 | 0 |
| Chickweed | 0 | 0 | 0 | 0 | 0 | 50 | 30 | 30 | 30 | 0 |
| Knotweed | 70 | 70 | 50 | 0 | 0 | — | — | — | — | — |
| Lambsquarters | 0 | 0 | 0 | 0 | 0 | — | 30 | 0 | 0 | 0 |
| Persian speedwell | 50 | 30 | 0 | 0 | 0 | 0 | 0 | 0 | 0 | 0 |
| Scentless chamomille | 60 | 0 | 0 | 0 | 0 | 100 | 90 | 80 | 80 | 80 |
| Sugar beet | 40 | 40 | 30 | 20 | 0 | 10 | 10 | 0 | 0 | 0 |
| Viola | 40 | 20 | 20 | 20 | 0 | 40 | 30 | 0 | 0 | 0 |
| Wheat | 30 | 20 | 20 | 20 | 20 | 50 | 30 | 30 | 30 | 0 |
| Wild buckwheat | 50 | 0 | 0 | 0 | 0 | 100 | 90 | 80 | 70 | 70 |
| Wild oat | 30 | 30 | 30 | 30 | 0 | 30 | 30 | 20 | 20 | 0 |
| RATE (g/ha) | | | | | | 250 | 125 | 64 | 32 | 16 |
| PREEMERGENCE | | | | | | | | | | |
| Blackgrass | | | | | | 30 | 30 | 0 | 0 | 0 |
| Catchweed bedstraw | | | | | | 0 | 0 | 0 | 0 | 0 |
| Chickweed | | | | | | 0 | 0 | 0 | 0 | 0 |
| Knotweed | | | | | | — | — | — | — | 0 |
| Lambsquarters | | | | | | 100 | 100 | 90 | 0 | 0 |
| Persian speedwell | | | | | | 0 | 0 | 0 | 0 | 0 |
| Scentless chamomille | | | | | | — | — | — | — | — |
| Sugar beet | | | | | | 0 | 0 | 0 | 0 | 0 |
| Viola | | | | | | 30 | 0 | 0 | 0 | 0 |
| Wheat | | | | | | 30 | 0 | 0 | 0 | 0 |
| Wild buckwheat | | | | | | 40 | 0 | 0 | 0 | 0 |
| Wild oat | | | | | | 40 | 0 | 0 | 0 | 0 |

| | Cmpd 13 | | | | Cmpd 15 | | | | |
|---|---|---|---|---|---|---|---|---|---|
| RATE (g/ha) | 64 | 32 | 16 | 8 | 125 | 64 | 32 | 16 | 8 |
| POSTEMERGENCE | | | | | | | | | |
| Blackgrass | 0 | 0 | 0 | 0 | 0 | 0 | 0 | 0 | 0 |
| Catchweed bedstraw | 0 | 0 | 0 | 0 | 0 | 0 | 0 | 0 | 0 |
| Chickweed | 20 | 0 | 0 | — | 0 | 0 | 0 | 0 | 0 |
| Knotweed | — | — | — | 0 | — | — | — | — | — |

TABLE C-continued

|  | | | | | | | | | |
|---|---|---|---|---|---|---|---|---|---|
| Lambsquarters | 100 | 100 | 100 | 50 | — | — | — | — | — |
| Persian speedwell | 50 | 50 | 30 | 30 | 100 | 0 | 0 | 0 | 0 |
| Scentless chamomille | 100 | 100 | 70 | 30 | 0 | 0 | 0 | 0 | 0 |
| Sugar beet | 0 | 0 | 0 | 0 | 30 | 20 | 0 | 0 | 0 |
| Viola | 0 | 0 | 0 | 0 | — | 0 | 0 | 0 | 0 |
| Wheat | 20 | 20 | 0 | 0 | 40 | 40 | 40 | 0 | 0 |
| Wild buckwheat | 80 | 70 | 0 | 0 | 100 | 0 | 0 | 0 | 0 |
| Wild oat | 30 | 30 | 20 | 0 | 30 | 0 | 0 | 0 | 0 |
| PREEMERGENCE | | | | | | | | | |
| Blackgrass |  | 0 |  | 0 |  | 0 | 0 | 0 |  |
| Catchweed bedstraw |  | 30 |  | 0 |  | 70 | 30 | 0 |  |
| Chickweed |  | 0 |  | 0 |  | 90 | 70 | 30 |  |
| Knotweed |  | — |  | — |  | 80 | — | — |  |
| Lambsquarters |  | 0 |  | — |  | — | — | — |  |
| Persian speedwell |  | 0 |  | 0 |  | 50 | 50 | 0 |  |
| Scentless chamomille |  | 0 |  | 0 |  | 20 | 20 | 0 |  |
| Sugar beet |  | 0 |  | 0 |  | 100 | 80 | 10 |  |
| Viola |  | 90 |  | 0 |  | 60 | 30 | 20 |  |
| Wheat |  | 20 |  | 0 |  | 80 | 60 | 50 |  |
| Wild buckwheat |  | 50 |  | 40 |  | 80 | 50 | 0 |  |
| Wild oat |  | 0 |  | 0 |  | 30 | 0 | 0 |  |

|  | Cmpd 19 | | | | Cmpd 31 | | | | |
|---|---|---|---|---|---|---|---|---|---|
| RATE (g/ha) | 32 | 16 | 8 | 4 | 250 | 125 | 64 | 32 | 16 |
| POSTEMERGENCE | | | | | | | | | |
| Blackgrass | 50 | 50 | 30 | 0 | 50 | 50 | 50 | 50 | 50 |
| Catchweed bedstraw | 90 | 90 | 70 | 0 | 100 | 100 | 70 | 30 | 30 |
| Chickweed | 100 | 90 | 70 | 30 | 80 | 70 | 50 | 50 | 50 |
| Knotweed | — | — | — | — | — | — | — | — | — |
| Lambsquarters | 100 | 100 | 100 | 100 | 100 | 100 | 100 | 100 | 100 |
| Persian speedwell | 30 | 0 | 0 | 0 | 0 | 0 | 0 | 0 | 0 |
| Scentless chamomille | 80 | 80 | 40 | 0 | 90 | 90 | 90 | 70 | 50 |
| Sugar beet | 90 | 50 | 50 | 30 | 80 | 50 | 10 | 0 | 0 |
| Viola | 30 | 0 | 0 | 0 | 80 | 30 | 30 | 30 | 0 |
| Wheat | 60 | 50 | 40 | 20 | 70 | 70 | 70 | 30 | 30 |
| Wild buckwheat | 100 | 100 | 0 | 0 | 100 | 100 | 90 | 70 | 50 |
| Wild oat | 30 | 30 | 0 | 0 | 50 | 40 | 40 | 40 | 20 |
| RATE (g/ha) | 125 | 64 | 32 | 16 | | | | | |
| PREEMERGENCE | | | | | | | | | |
| Blackgrass | 80 | 70 | 70 | 70 | 70 | 70 | 30 | 30 | 0 |
| Catchweed bedstraw | 100 | 80 | 80 | 30 | 70 | 50 | 20 | 0 | 0 |
| Chickweed | 100 | 100 | 90 | 90 | 0 | 0 | 0 | 0 | 0 |
| Knotweed | 100 | 100 | 100 | 100 | — | — | — | — | — |
| Lambsquarters | 100 | 100 | 100 | 100 | 100 | 100 | 100 | 90 | 90 |
| Persian speedwell | 70 | 40 | 0 | 0 | 0 | 0 | 0 | 0 | 0 |
| Scentless chamomille | 100 | 90 | 90 | 90 | — | — | — | — | — |
| Sugar beet | 90 | 90 | 80 | 80 | 0 | 0 | 0 | 0 | 0 |
| Viola | 90 | 90 | 90 | 80 | 40 | 30 | 30 | 30 | 0 |
| Wheat | 80 | 50 | 30 | 10 | 50 | 40 | 30 | 30 | 30 |
| Wild buckwheat | 90 | 90 | 90 | 50 | 100 | 80 | 40 | 30 | 30 |
| Wild oat | 70 | 60 | 30 | 30 | 40 | 40 | 30 | 0 | 0 |

What is claimed is:

1. A compound of the formula:

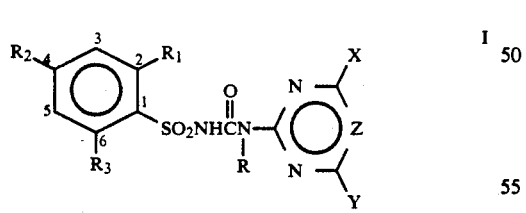

wherein
R is H or $CH_3$;
$R_1$ is $NO_2$, $CO_2R_4$, $C(O)R_5$, $S(O)_2R_6$,

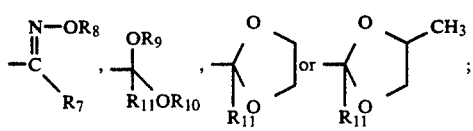

$R_2$ is $$-CHR_{13}, -NH, -NOH$$
$$\quad\ \ \ |\qquad\ \ \ |\qquad\ \ \ |$$
$$\quad\ \ R_{12}\quad\ R_{14}\quad\ R_{15}$$

or CHO;
$R_3$ is H, $OCH_3$, $CH_3$ or Cl;
$R_4$ is $C_1$-$C_3$ alkyl, $C_2$-$C_4$ alkoxyalkyl, $C_2$-$C_3$ haloalkyl, allyl or propargyl;
$R_5$ is $C_1$-$C_3$ alkyl, $C_2$-$C_4$ alkoxyalkyl, $C_3$-$C_4$ cycloalkyl or cyclopropylmethyl;
$R_6$ is $C_1$-$C_3$ alkyl or $C_2$-$C_4$ alkoxyalkyl;
$R_7$ is $C_1$-$C_3$ alkyl, $C_2$-$C_4$ alkoxyalkyl, $C_3$-$C_4$ cycloalkyl, cyclopropylmethyl, $C_1$-$C_2$ alkoxy, CN or Cl;
$R_8$ is $C_1$-$C_3$ alkyl;
$R_9$ and $R_{10}$ are independently $C_1$-$C_2$ alkyl;
$R_{11}$ is H or $CH_3$;
$R_{12}$ is H or $CH_3$;
$R_{13}$ is CN, SCN, $NH_2$, $NHCH_3$, $N(CH_3)_2$, $NHC(O)CH_3$ or $W_2R_{16}$;
$R_{14}$ is $C_1$-$C_3$ alkyl, $C_2$-$C_4$ alkoxyalkyl or $C_2$-$C_3$ haloalkyl;

$R_{15}$ is H, $C_1$–$C_3$ alkyl, $C_2$–$C_4$ alkoxyalkyl or $C_2$–$C_3$ haloalkyl;

$R_{16}$ is H, $C_1$–$C_6$ alkyl, $C_3$–$C_4$ cycloalkyl or $C_4$–$C_5$ cycloalkylalkyl;

$W_2$ is O or S;

X is $C_1$–$C_2$ alkyl, $OCH_3$, Cl, or $OCF_2H$;

Y is H, $CH_3$, $C_1$–$C_2$ alkoxy, $NHCH_3$, or $N(CH_3)_2$; and

Z is CH;

and their agriculturally suitable salts; provided that
1) when X is Cl, then Y is $OCH_3$, $OC_2H_5$, $NHCH_3$, or $N(CH_3)_2$;
2) when X is $OCF_2H$, then $R_2$ is

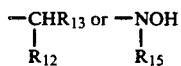

3) when $R_2$ is

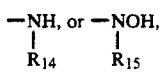

then $R_1$ is $CO_2R_4$;
4) When $R_{16}$ is H, $W_2$ is O.

2. A compound of claim 1 wherein
R is H and $R_3$ is H.

3. A compound of claim 2 wherein
$R_4$ is $CH_3$, $CH_2CH_3$ or $CH_2OCH_3$;
$R_5$ is $C_1$–$C_3$ alkyl, cyclopropyl, cyclopropylmethyl or $CH_2OCH_3$;
$R_6$ is $C_1$–$C_3$ alkyl or $CH_2OCH_3$;
$R_7$ is $C_1$–$C_3$ alkyl, cyclopropyl, cyclopropylmethyl or $CH_2OCH_3$; and
$R_{16}$ is H or $C_1$–$C_3$ alkyl.

4. The compound of claim 1 which is methyl 2-[[[[(4,6-dimethoxypyrimidin-2-yl)amino]carbonyl]amino]sulfonyl]-5-(methoxymethyl)benzoate.

5. The compound of claim 1 which is methyl 2-[[[[(4,6-dimethoxypyrimidin-2-yl)amino]carbonyl]amino]sulfonyl]-5-(hydroxymethyl)benzoate.

6. A compound of claim 3 where $R_2$ is

7. A compound of claim 6 where $R_{13}$ is $W_2R_{16}$.
8. A compound of claim 3 where $R_2$ is $NHR_{14}$.
9. A compound of claim 3 where $R_2$ is

10. A compound of claim 3 where $R_2$ is CHO.

11. A composition suitable for controlling the growth of undesired vegetation which comprises an effective amount of a compound of claim 1 and at least one of the following: surfactant, solid diluent or liquid diluent.

12. A composition suitable for controlling the growth of undesired vegetation which comprises an effective amount of a compound of claim 2 and at least one of the following: surfactant, solid diluent or liquid diluent.

13. A composition suitable for controlling the growth of undesired vegetation which comprises an effective amount of a compound of claim 3 and at least one of the following: surfactant, solid diluent or liquid diluent.

14. A composition suitable for controlling the growth of undesired vegetation which comprises an effective amount of a compound of claim 4 and at least one of the following: surfactant, solid diluent or liquid diluent.

15. A composition suitable for controlling the growth of undesired vegetation which comprises an effective amount of a compound of claim 5 and at least one of the following: surfactant, solid diluent or liquid diluent.

16. A composition suitable for controlling the growth of undesired vegetation which comprises an effective amount of a compound of claim 6 and at least one of the following: surfactant, solid diluent or liquid diluent.

17. A composition suitable for controlling the growth of undesired vegetation which comprises an effective amount of a compound of claim 7 and at least one of the following: surfactant, solid diluent or liquid diluent.

18. A composition suitable for controlling the growth of undesired vegetation which comprises an effective amount of a compound of claim 8 and at least one of the following: surfactant, solid diluent or liquid diluent.

19. A composition suitable for controlling the growth of undesired vegetation which comprises an effective amount of a compound of claim 9 and at least one of the following: surfactant, solid diluent or liquid diluent.

20. A composition suitable for controlling the growth of undesired vegetation which comprises an effective amount of a compound of claim 10 and at least one of the following: surfactant, solid diluent or liquid diluent.

21. A method for controlling the growth of undesired vegetation which comprises applying to the locus to be protected an effective amount of a compound of claim 1.

22. A method for controlling the growth of undesired vegetation which comprises applying to the locus to be protected an effective amount of a compound of claim 2.

23. A method for controlling the growth of undesired vegetation which comprises applying to the locus to be protected an effective amount of a compound of claim 3.

24. A method for controlling the growth of undesired vegetation which comprises applying to the locus to be protected an effective amount of a compound of claim 4.

25. A method for controlling the growth of undesired vegetation which comprises applying to the locus to be protected an effective amount of a compound of claim 5.

26. A method for controlling the growth of undesired vegetation which comprises applying to the locus to be protected an effective amount of a compound of claim 6.

27. A method for controlling the growth of undesired vegetation which comprises applying to the locus to be protected an effective amount of a compound of claim 7.

28. A method for controlling undesired vegetation in sugarbeets which comprises applying to the locus of the sugarbeets an effective amount of the compound of claim 4.

29. A method for controlling undesired vegetation in sugarbeets which comprises applying to the locus of the sugarbeets an effective amount of the compound of claim 5.

30. A method for controlling undesired vegetation in sugarbeets which comprises applying to the locus of the sugarbeets an effective amount of the compound of claim 6.

31. A method for controlling undesired vegetation in sugarbeets which comprises applying to the locus of the sugarbeets an effective amount of the compound of claim 7.

32. A method for controlling undesired vegetation in sugarbeets which comprises applying to the locus of the sugarbeets an effective amount of the compound of claim 8.

33. A method for controlling undesired vegetation in sugarbeets which comprises applying to the locus of the sugarbeets an effective amount of the compound of claim 9.

34. A method for controlling undesired vegetation in sugarbeets which comprises applying to the locus of the sugarbeets an effective amount of the compound of claim 10.

* * * * *